United States Patent [19]

Kolesnick

[11] Patent Number: 5,451,518
[45] Date of Patent: Sep. 19, 1995

[54] PURIFIED HUMAN CERAMIDE-ACTIVATED PROTEIN KINASE

[75] Inventor: Richard N. Kolesnick, New York, N.Y.

[73] Assignee: Sloan-Kettering Institute for Cancer Research, New York, N.Y.

[21] Appl. No.: 976,378

[22] Filed: Nov. 13, 1992

[51] Int. Cl.⁶ ............................ C12N 9/12; C12Q 1/48; A61K 38/45
[52] U.S. Cl. ................................. 435/194; 424/94.5; 435/15
[58] Field of Search .................. 435/194, 15; 424/94.5

[56] References Cited

PUBLICATIONS

Chan (1987) *J. Biol. Chem.*, 262(5), 2415–2422.
Mathias et al. (15 Nov. 1991) *Proc. Nat. Acad. Sci. U.S.A.*, 88(22), 10009–10013.
Veldhoven et al. (1992) *Biochem. Biophys. Res. Comm.*, 187(1), 209–216.

*Primary Examiner*—Marian C. Knode
*Assistant Examiner*—Jon P. Weber
*Attorney, Agent, or Firm*—John P. White

[57] ABSTRACT

A membrane-bound ceramide-activated protein kinase has been purified from human cells. The protein kinase has an apparent molecular weight of about 95 kD and specifically phosphorylates the threonine residue in a polypeptide containing Pro-Leu-Thr-Pro (SEQ ID NO:1).

1 Claim, 15 Drawing Sheets

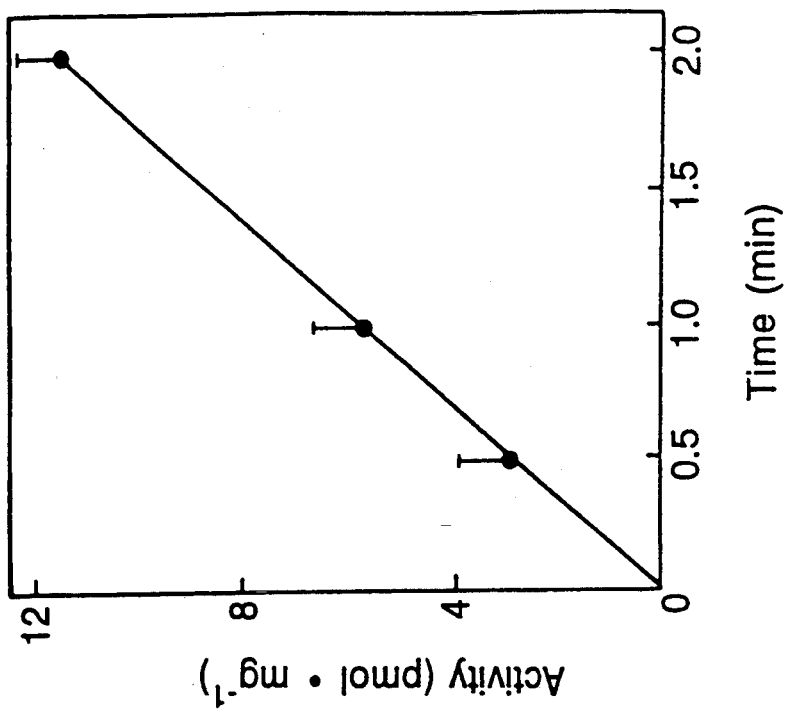
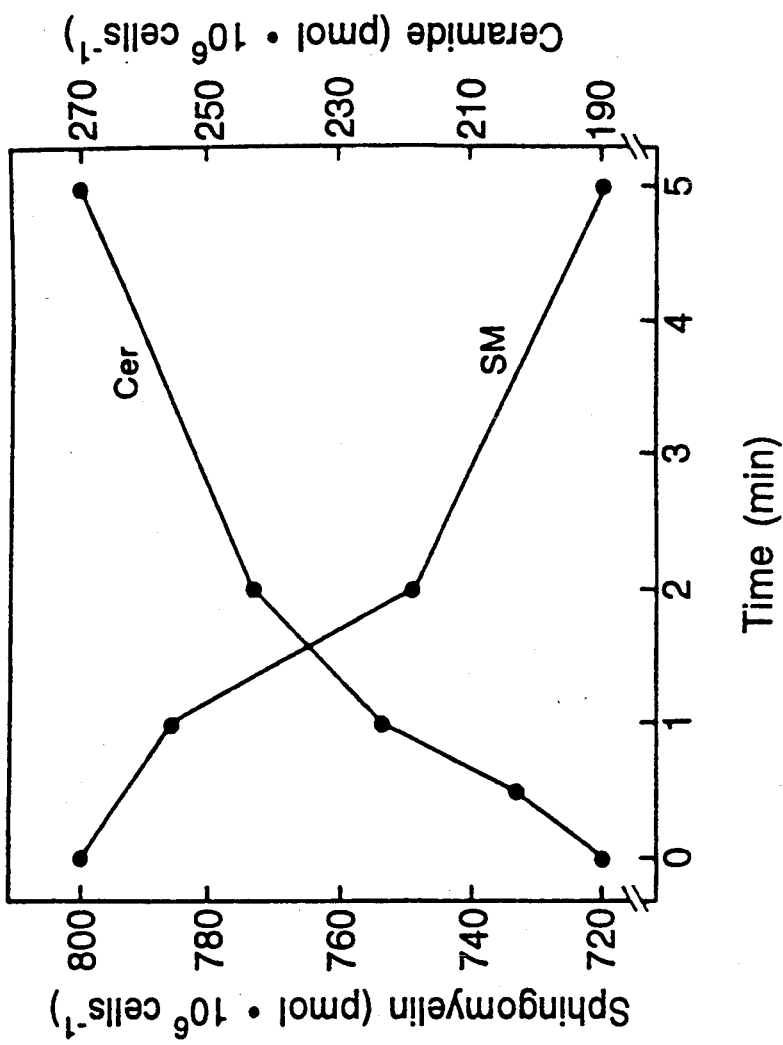

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 4 amino acids
      ( B ) TYPE: amino acid
      ( C ) STRANDEDNESS: unknown
      ( D ) TOPOLOGY: unknown ( i i ) MOLECULE TYPE: protein ( v i ) ORIGINAL SOURCE:
      ( A ) ORGANISM: homo sapien ( x i ) SEQUENCE DESCRIPTION: SEQ ID NO:1:

Pro  Leu  Thr  Pro
   1

( 2 ) INFORMATION FOR SEQ ID NO:2:

( i ) SEQUENCE CHARACTERISTICS:
      ( A ) LENGTH: 19 amino acids
      ( B ) TYPE: amino acid
      ( C ) STRANDEDNESS: unknown
      ( D ) TOPOLOGY: unknown ( i i ) MOLECULE TYPE: protein ( v i ) ORIGINAL SOURCE:
      ( A ) ORGANISM: homo sapien ( x i ) SEQUENCE DESCRIPTION: SEQ ID NO:2:

Glu  Leu  Val  Glu  Pro  Leu  Thr  Pro  Ser  Gly  Glu  Ala  Pro  Asn  Gln
   1                 5                           10                          15

Ala  Leu  Leu  Arg

PURIFIED HUMAN CERAMIDE-ACTIVATED PROTEIN KINASE

This invention was made with support under Grant Nos. RO1-CA-42385 and CA-09512-06 from the National Institute of Health. Accordingly, the United States government has certain rights in the invention.

BACKGROUND OF THE INVENTION

Throughout this application, various publications are referenced by Arabic numerals. Full citations for these references may be found at the end of the specification immediately preceding the claims. The disclosure of these publications is hereby incorporated by reference into this application to describe more fully the art to which this invention pertains.

Recent investigations have identified a metabolic pathway involving sphingomyelin and derivatives that may be involved in signal transduction (1-8). This pathway is initiated by the hydrolysis of sphingomyelin to ceramide via the action of a sphingomyelinase. Ceramide may then be deacylated to sphingoid bases, putative inhibitors of protein kinase C (9-12), or phosphorylated to the sphingolipid ceramide 1-phosphate by the action of a recently described calcium-dependent ceramide kinase (4, 5, 13). The biologic role of ceramide 1-phosphate and regulation of the kinase that mediates its synthesis have not yet been determined. This pathway appears specific for ceramide derived from sphingomyelin, as ceramide derived from glycosphingolipids is not converted either to sphingoid bases (14) or to ceramide 1-phosphate (4). Recently, Hannun and coworkers (6-8) have provided evidence that this sphingomyelin pathway may be involved in signal transduction. Tumor necrosis factor (TNF) $\alpha$, $\gamma$ interferon, and 1,25-dihydroxyvitamin $D_3$, factors that induce monocytic differentiation of HL-60 promyelocytic cells, all stimulate sphingomyelin degradation to ceramide as an early event in cellular activation (6-8). A synthetic ceramide N-acetylsphingosine could replace these agents in induction of monocytic differentiation of these cells. Furthermore, there have also been numerous reports that TNF and IL-1 stimulate a common set of events in diverse biological systems (60).

Direct evidence for second-messenger function for ceramide has also been shown. Davis and coworkers (15-17) originally showed that sphingosine induced epidermal growth factor receptor (EGFR) phosphorylation on Thr-669 in A-431 human epidermoid carcinoma cells by a mechanism that did not involve protein kinase C. It was demonstrated that sphingosine was rapidly converted to ceramide by these cells and that ceramide induced identical phosphorylation (18). These studies were interpreted as evidence that ceramide had bioeffector properties, and might mediate, in part, the action of exogenous sphingosine. However, prior to the subject invention, no kinass was identified capable of mediating the effects of ceramide as a second messenger.

The subject invention provides a purified ceramideactivated protein kinase which functions as a key element in a sphingomyelin pathway utilizing ceramide as a second messenger. The knowledge that a ceramideactivated protein kinase exists as part of the sphingomyelin pathway enables the treatment of certain disorders by selectively modifying the function of this kinase in appropriate cells. Such disorders where this approach is possible include, by way of example, HIV infection, inflammatory disorders and disorders associated with poor stem cell growth. Accordingly, the subject invention provides methods of treating subjects having such disorders with agents capable of modifying the activity of ceramide-activated protein kinase, and methods of identifying such agents.

SUMMARY OF THE INVENTION

The subject invention provides a purified membrane-bound ceramide-activated protein kinase having an apparent molecular weight of about 95 kD which is capable of specifically phosphorylating the threonine residue in a Pro-Leu-Thr-Pro-(SEQID NO: 1) containing polypeptide.

The subject invention also provides a method of determining whether an agent is capable of specifically inhibiting the phosphorylation activity of the ceramide-activated protein kinase of the subject invention which comprises: (a) contacting the protein kinase with a predetermined amount of a polypeptide containing the amino acid sequence Pro-Leu-Thr-Pro(SEQID NO: 1), and the agent, under conditions i) which would permit activity of the protein kinase to be linear with respect to time and protein kinase concentration in the absence of the agent, and ii) which would permit the specific phosphorylation by the protein kinase of a predetermined number of the threonine residues in such predetermined amount of the Pro-Leu-Thr-Pro-(SEQID NO: 1) containing polypeptide in the absence of the agent; (b) quantitatively determining the percentage of such predetermined number of threonine residues which are specifically phosphorylated in the presence of the agent, thereby determining whether the agent is capable of inhibiting the activity of the ceramide-activated protein kinase; and (c) determining whether the agent inhibits the activity of a non-ceramide-activated kinase, so as to determine whether the agent is capable of specifically inhibiting the activity of the ceramide-activated protein kinase.

The subject invention further provides a method of determining whether an agent is capable of specifically stimulatingthe phosphorylation activity of the ceramide-activated protein kinase of the subject invention which comprises: (a) contacting the protein kinase with a predetermined amount of a polypeptide containing the amino acid sequence Pro-Leu-Thr-Pro(SEQID NO: 1), and the agent, under conditions i) which would permit activity of the protein kinase to be linear with respect to time and protein kinase concentration in the absence of the agent, and ii) which would permit the specific phosphorylation by the protein kinase of a predetermined number of the threonine residues in such predetermined amount of the Pro-Leu-Thr-Pro-(SEQID NO: 1) containing polypeptide in the absence of the agent; (b) quantitatively determining the percentage of such predetermined number of threonine residues which are specifically phosphorylated in the presence of the agent, thereby determining whether the agent is capable of stimulating the activity of the ceramide-activated protein kinase; and (c) determining whether the agent stimulates the activity of a non-ceramide-activated kinase, so as to determine whether the agent is capable of specifically stimulating the activity of the ceramide-activated protein kinase.

The subject invention further provides a method of treating a subject having an inflammatory disorder which comprises administering to the subject an agent capable of inhibiting the phosphorylation activity of a ceramide-activated protein kinase of T helper cells and macrophage cells of the subject in an amount effective to inhibit said phosphorylation activity, thereby reducing the inflammation associated with the disorder.

The subject invention further provides a method of treating a human subject infected with HIV so as to reduce the proliferation of HIV in the human subject which comprises administering to the human subject an agent capable of inhibiting the phosphorylation activity of a ceramide-activated protein kinase of the HIV-infected cells of the human subject in an amount effective to inhibit said activity, thereby reducing the proliferation of HIV in the human subject.

Finally, the subject invention provides a method of treating a subject having a disorder associated with poor stem cell growth, which comprises administering to the subject an agent capable of stimulating the phosphorylation activity of a ceramide-activated protein kinase of the stem cells of the subject in an amount effective to stimulate said phosphorylation activity, thereby stimulating stem cell growth.

Figure 1:
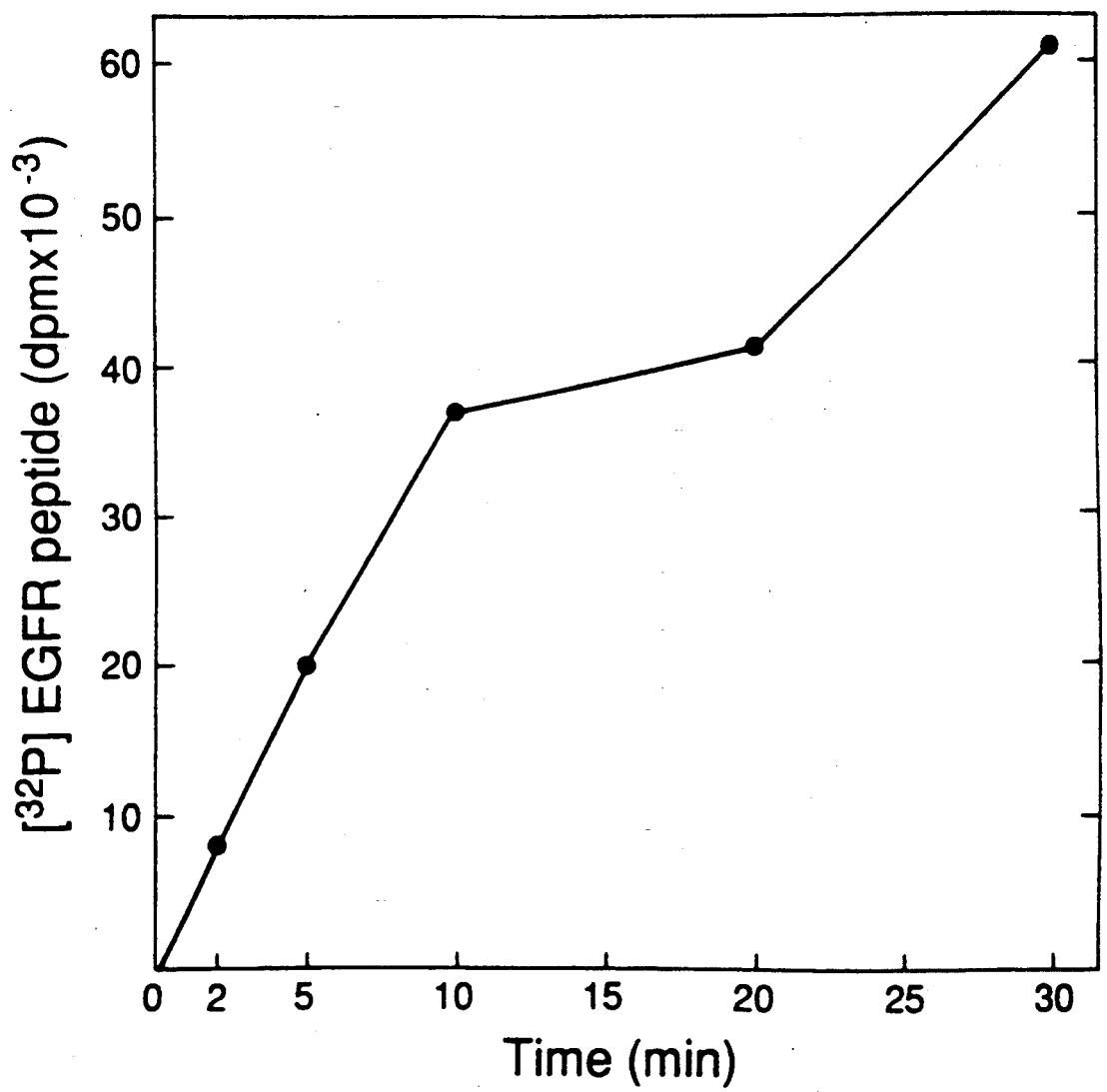
FIGURE 1

Kinetics of $^{32}P_i$ incorporation into the EGFR peptide

Peptide phosphorylation was done in a reaction mixture containing 25 μl of postnuclear supernatant (220 μg of protein) from A-431 cells, 50 μl of EGFR peptide (4 mg/ml in 25 mM Hepes, pH 7.4), and 125 μl of reaction buffer (50 mM Hepes, pH 7.4/20 mM MgCl$_2$). The reaction was initiated by addition of 50 μl of [γ-$^{32}$P]ATP (150 μM final concentration) and terminated by addition of 50 μl of 0.5 M ATP in 90% (vol/vol) formic acid. Samples were spotted on phosphocellulose paper, washed with 1M acetic acid/4 mM pyrophosphate, and $^{32}$P incorporation was measured by liquid-scintillation counting, as described (17, 25). A boiled protein blank was subtracted from each data value. The data (means) represent duplicate samples from one of two similar experiments.

FIGURE 2

Mg$^{2+}$ concentration-dependence of EGFR peptide phosphorylation

These studies were done as described for FIG. 1, using microsomal membrane (7.5 μg/μl) as the source of kinase activity. Reaction mixtures received various concentrations of Mg$^{2+}$ (0.1-25 mM final concentration), and reactions were terminated at 2 minutes. Phosphorylated peptide was isolated by HPLC and quantified by Cerenkov counting. The dimensions of velocity (V) are pmol.min$^{-1}$/mg of protein$^{-1}$. Data represent values derived from one of three similar experiments.

FIGURE 3

Identification of phosphorylated EGFR peptide

Figure 2:
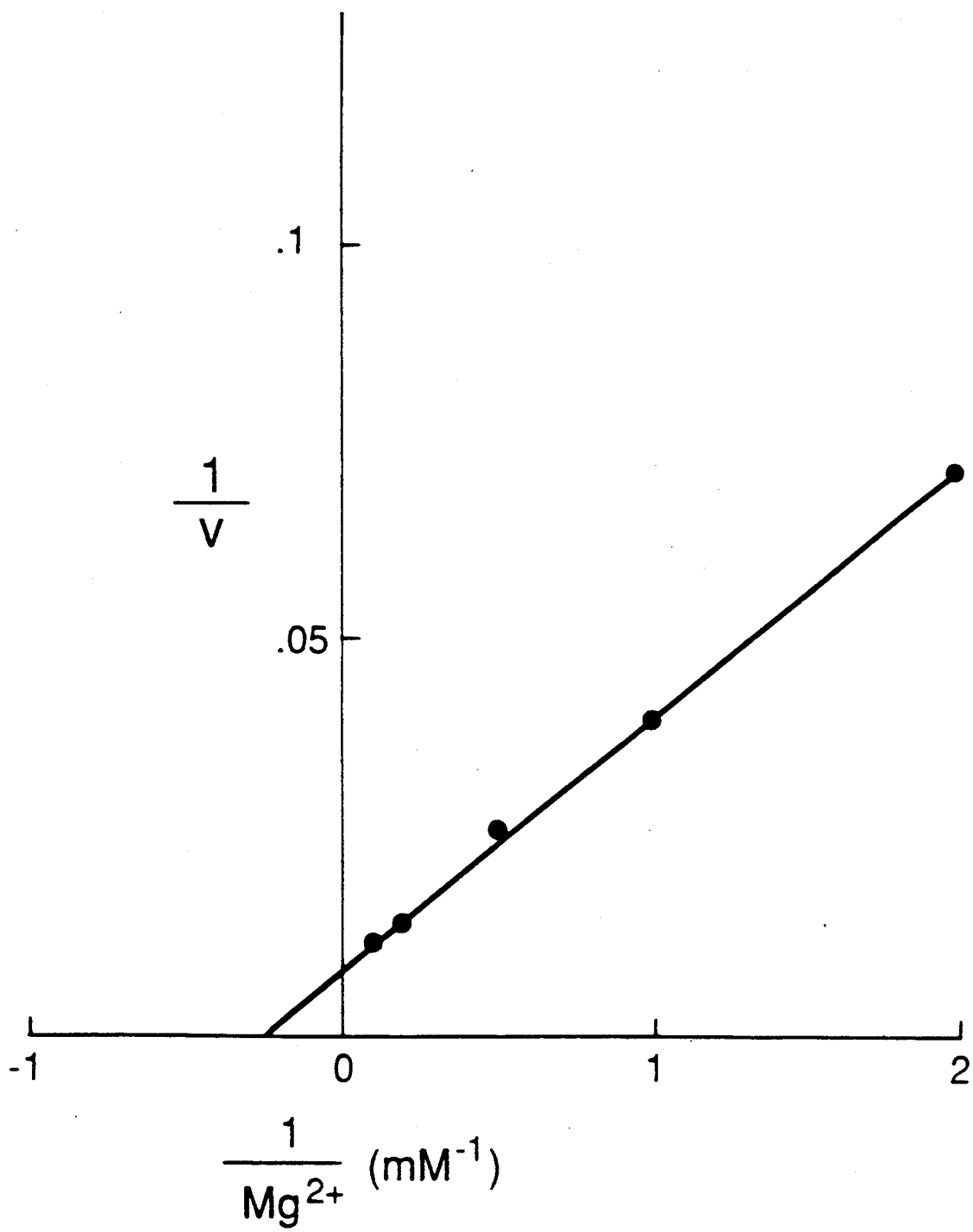

Reactions were done, and phosphorylated peptide was quantified as for FIG. 2. (Left) HPLC elution profile of samples with or without the EGFR peptide. (Right) Phosphoamino acid analysis of the phosphorylated peptide purified by HPLC. Phosphorylated amino acids (Y, tyrosinase; T, threonine; S, serine) were resolved by one-dimensional thin-layer electrophoresis and identified by ninhydrin staining of carrier phosphoamino acids and autoradiography.

FIGURE 4

Kinetics of ceramide-induced $^{32}P_i$ incorporation into EGFR peptide

Peptide phosphorylation was done as described in FIG. 2 in the absence (○) or presence ( ) of 0.5 μM C$_8$-ceramide. Phosphorylated peptide was resolved by HPLC. Values (means) represent data from three experiments.

FIGURE 5

Concentration-dependence of ceramide-induced $^{32}P_i$ incorporation into EGFR peptide Peptide phosphorylation reactions were done as described for FIG. 2, for 2 minutes, using various concentrations of ceramide (0.001-3 μM). Phosphorylated peptide was resolved by HPLC. Values (means) represent data from three experiments.

FIGURE 6

Figure 5:
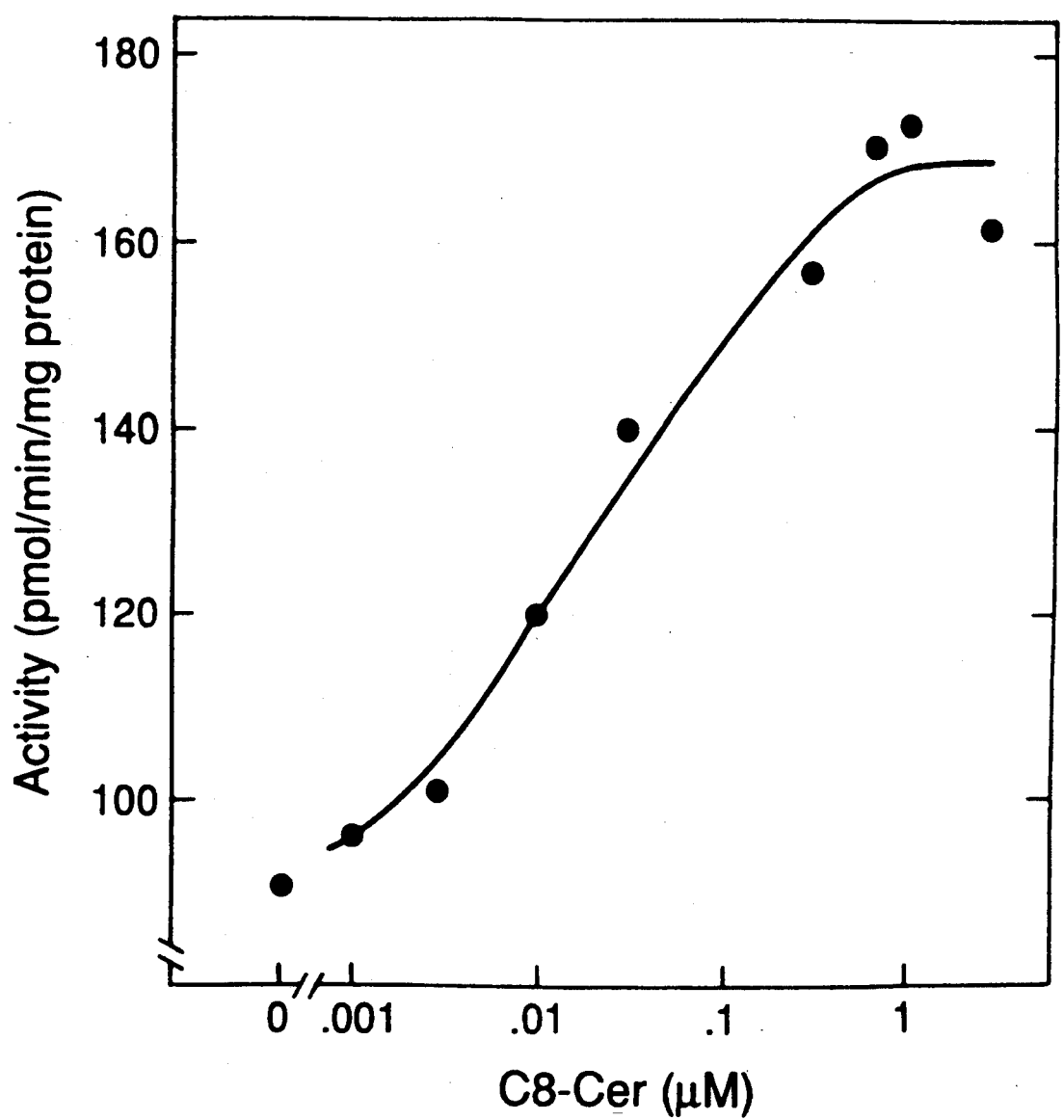

Concentration-dependence of sphingosine-induced $^{32}P_i$ incorporation into EGFR peptide Peptide phosphorylation reactions were done and analyzed as described in FIG. 5, using various concentrations of sphingosine (0.001-3 μM). Values (means) represent data from two experiments.

FIGURE 7

Kinetics of TNF-α-induced $^{32}P_i$ incorporation into EGFR pepide

HL-60 cells were resuspended in RPMI 1640 medium (1×10$^6$ cells per ml) containing 1% FBS for 2 hours before stimulation with TNF-α (30 nM). At the indicated times, cells were centrifuged at 500×g for 5 minutes, and the cell pellet was homogenized in buffer, as described. Portions of a microsomal membrane fraction were used in the kinase assay, as described for FIG. 2. Values (means) represent data derived from two separate experiments.

FIGURE 8

Figure 7:
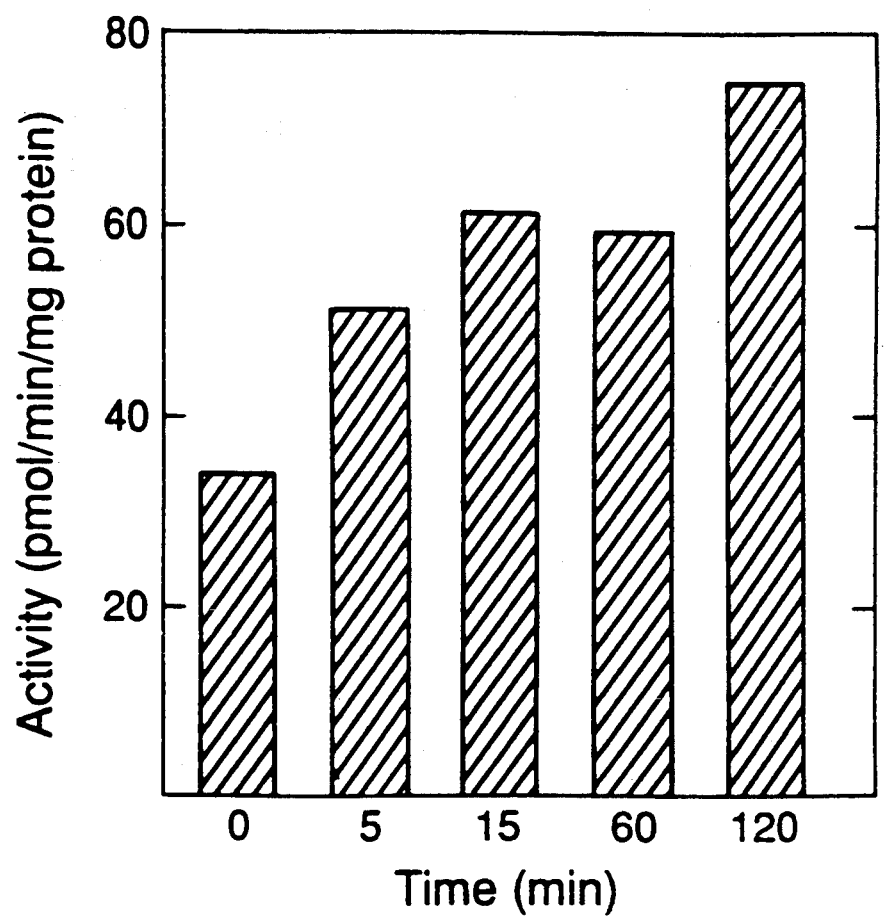

Concentration-dependence of TNF-α-induced $^{32}P_i$ incorporation into EGFR peptide These studies were done as described for FIG. 7 with various concentrations of TNF-α for 60 minutes of stimulation. Values (means) represent data derived from two separate experiments.

FIGURES 9A AND 9B

TNF-α effects on sphingomyelin (FIG. 9A) and ceramide (FIG. 9B) concentrations in a cell-free system HL-60 cells were grown in RPMI 1640 medium supplemented with 10% bovine calf serum and amino acids (4). To measure sphingomyelin, cells were resuspended (1×10$^6$ ml$^{-1}$), labeled for 48 hours in medium with [$^3$H]choline (1 μCi ml$^{-1}$) (57), in serum-free medium containing bovine insulin (5 μg ml$^{-1}$) and human transferrin (5 μg ml$^{-1}$). After 3 hours, cells were resuspended (150×10$^6$ ml$^{-1}$) in homogenization buffer (50 mM NaF, 5 mM EGTA, and 25 mM Hepes, pH 7.4), disrupted at 4° C. with 150 strokes of a tight-fitting Dounce homogenizer (Fisher Scientific, Pittsburgh, Pa.), and centrifuged for 5 minutes (500 g). The nuclei-free supernate was first incubated for 5 minutes at 4° C. with 30 nM human TNF-α (Genentech, South San Francisco, Calif.) or diluent (50 mMHepes, pH 7.4). At time zero, 15 μl of supernate (112 μg per incubation) were added to a reaction mixture containing 30 μl of 25 mM Hepes, pH 7.4, 30 μl of 750 μM ATP, and 75 μl of reaction buffer (50 mM Hepes, pH 7.4 and 20 mM $MgCl_2$) at 22° C. The reaction was terminated with $CHCl_3:CH_3OH:HCl$ (100:100:1, v/v/v) (3, 4, 13) and 150 μl of balanced salt solution (135 mM NaCl, 4.5 mM KCl, 1.5 mM $CaCl_2$, 0.5 mM $MgCl_2$, 5.6 mM glucose, and 10 mM Hepes, pH 7.2) containing 20 mM EDTA. Lipids in the organic phase extract were subjected to alkaline methanolysis to remove glycerophospholipids (4). Sphingomyelin recovery in the nuclei-free supernate was 93% of that in intact cells. A measure of $10^6$ cell equivalents of supernate contained 50 μg of protein. Sphingomyelin was resolved by thin-layer chromatograhy (TLC) with $CHCl_3:CH_3OH:CH_3COOH:H_2O$ (25:15:4:1.5) as solvent, identified by iodine vapor staining and quantified by liquid scintillation spectrometry (1, 8, 56). Ceramide was quantified with the diacylglycerol kinase reaction (4, 57). Values (mean) are derived from triplicate determinations from one experiment representative of three similar studies for sphingomyelin and four similar studies for ceramide.

FIGURES 10A AND 10B

Effect of TNF-α on ceramide-activated protein kinase activity

Figure 9B:
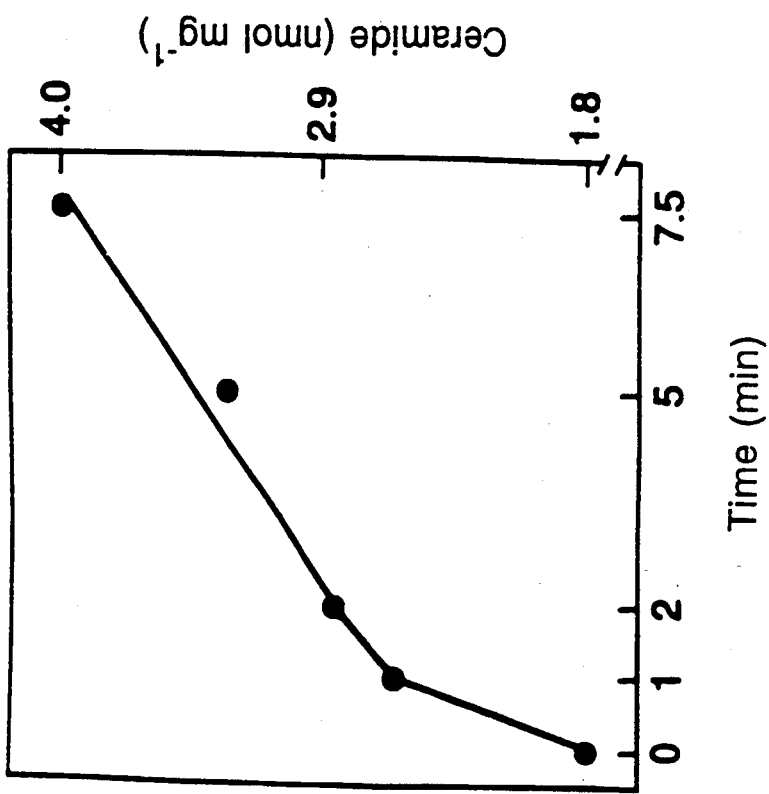
Figure 9A:
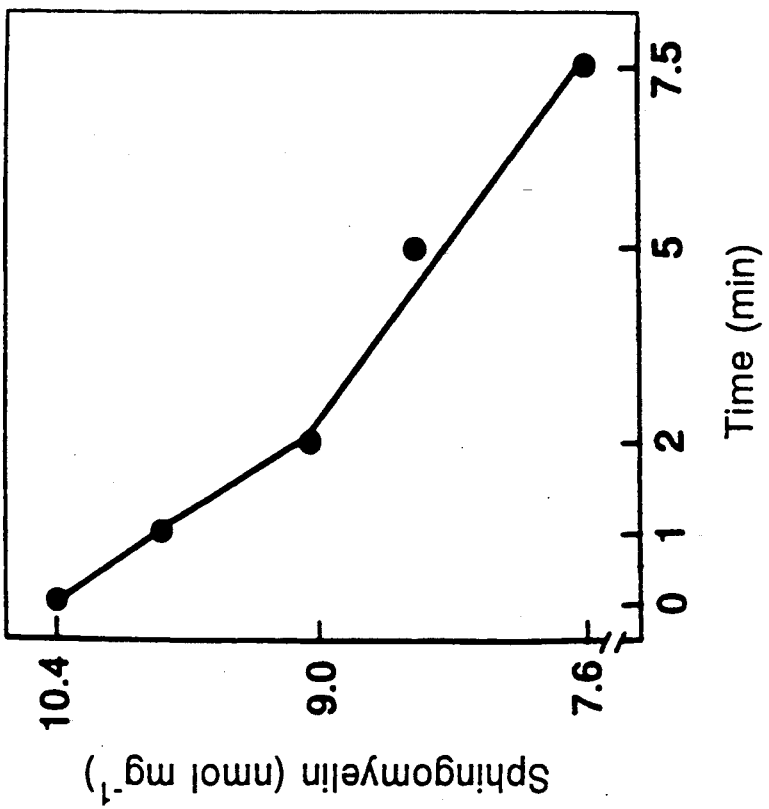

HL-60 cells were incubated in serum-free medium and homogenized (as in FIGS. 9A and 9B). After an initial incubation with TNF-α, 15 μl of nuclei-free supernate (112 μg per incubation) were added to a reaction mixture containing 30 μl of EGFR peptide (4 mg $ml^{-1}$ in 25 mM Hepes, pH 7.4), 30 μl of [γ-$P^{32}$] ATP (750 μM, 4000 dpm $pmol^{-1}$), and 75 μl of reaction buffer (40). The reaction was terminated by adding 30 μl of 0.5M ATP in 90% formic acid. Phosphorylated peptide was first run on a $C_{18}$ Sep-Pak cartridge, then resolved by $C_{18}$ reverse-phase HPLC (Waters, Milford, Mass.), with a linear gradient of acetonitrile. The peptide eluted at 30% acetonitrile, as determined by monitoring Cerenkov radiation in 1-ml fractions. Background activity was subtracted from each point. (FIG. 10A) Kinetics of TNF-α (30 nM)-stimulated EGFR peptide phosphorylation. Values (mean) represent data from four experiments. (FIG. 10B) Concentration dependence of EGFR peptide phosphorylation at 5 minutes of stimulation with TNF-α (0.01 to 30 nM). Values (mean) represent data derived from duplicate points in two experiments. The SEM of the values in (FIG. 10A) was 18% and the mean range of values in (FIG. 10B) was 3%.

FIGURE 11

Effect of phospholipases on ceramide-activated protein kinase activity

Nuclei-free supernates, prepared as in FIGS. 9A and 9B, were first incubated with TNF-α (3 nM) or added directly to reaction mixtures that contained various phospholipases; sphingomyelinase (SMase) ($1 \times 10^{-3}$ U $ml^{-1}$, S, aureus), phospholipase A2 (PlA2) ($3.8 \times 10^{-2}$ and $3.8 \times 10^{-1}$ U $ml^{-1}$, Vipera ruselli), phospholipase C (PLC) ($3.8 \times 10^{-2}$) U $ml^{-1}$, Bacillus cereus) and phospholipase D (PLD) ($3.8 \times 10^{-2}$ U $ml^{-1}$, Streptomyces chromocuscus). Peptide phosphorylation was measured as in FIGS. 10A nad 10B. Control value represents peptide phosphorylation in the absence of phospholipases or TNF-α. Values (mean ± SEM) represent data derived from duplicate samples in three experiments. *P<0.001 compared to control.

FIGURES 12A AND 12B

IL-1β effects on sphingomyelin levels in EL4 cells

Figure 12B:
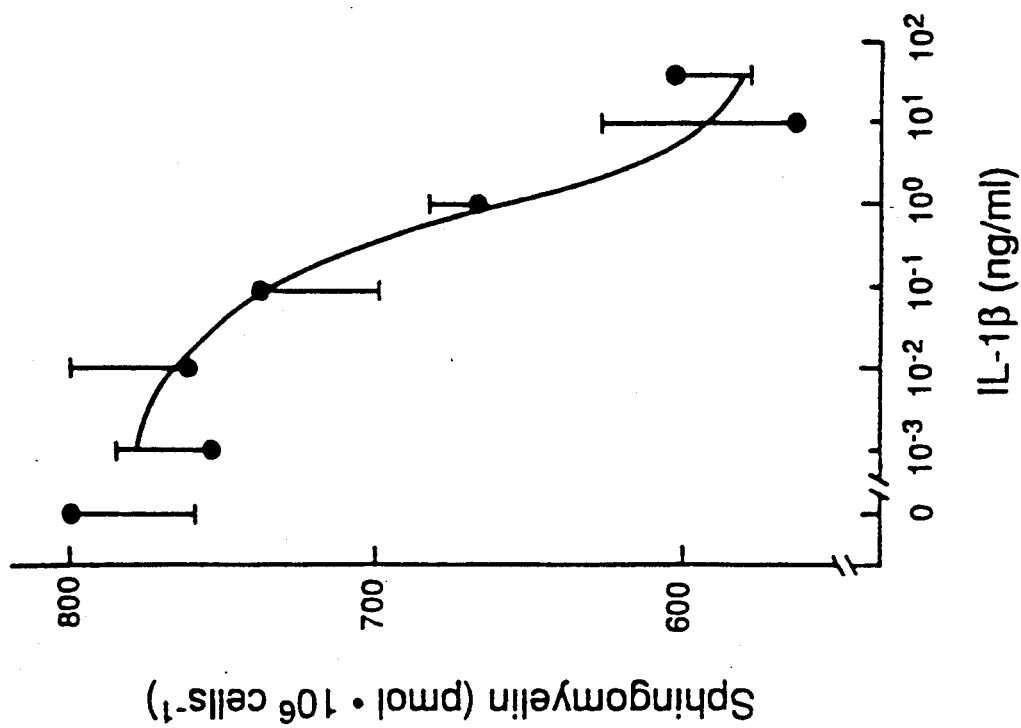

Time course (FIG. 12A) and dose response (FIG. 12B). Cells were grown to growth arrest ($1-1.5 \times 10^6$ cells $ml^{-1}$) in DME/Ham's F12 medium (1:1, v/v) containing 10% horse serum and for 48 hours [$^3$H]choline (1 μCi $ml^{-1}$). On the day of an experiment, cells were resuspended back into the same medium at $10 \times 10^6$ cells $ml^{-1}$ and stimulated with 40 ng $ml^{-1}$ IL-1β for the indicated times (FIG. 12A) or for 30 minutes with increasing concentrations of IL-1β (FIG. 12B). Human IL-1β may be obtained using methods well knownto those skilled in the art. Reactions were terminated with $CHCl_3:CH_3OH:HCl$ (100:100:1) containing 10 mM EDTA (82). Lipids in the organic phase extract were dried under $N_2$ and subjected to mild alkaline hydrolysis (0.1M methanolic KOH for 1 hour at 37° C.) to remove glycerophospholipids. Spingomyelin was resolved by thin-layer chromatography (TLC) using $CHCl_3:CH_3OH:CH_3COOH:H_2O$ (60:30:8:5) as solvent, identified by iodine vapor staining, and quantified by liquid scintillation spectrometry. As previously reported, the use of [$^3$H]choline as a measure of sphingomyelin content was validated by simultaneous phospholipid phosphorus measurements (62). Each value represents the mean ± SEM of triplicate determinations from four experiments in (FIG. 12A), and one representative of four similar studies performed in triplicate in (FIG. 12B).

FIGURE 13

Effect of IL-1β on ceramide levels in EL-4 cells

Figure 12A:
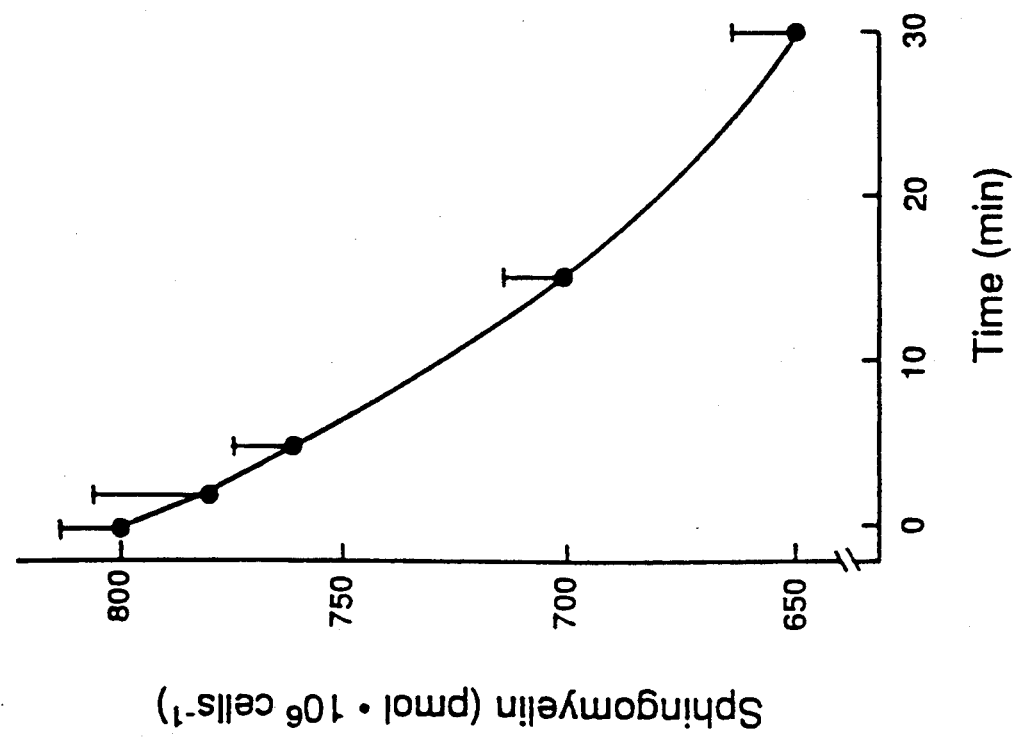

Cells were stimulated as in FIGS. 12A and 12B with IL-1β (40 ng $ml^{-1}$) and ceramide contained within the organic phase extract quantified enzymatically using the E. coli diacylglycerol kinase reaction (57). Lipids were resolved by TLC using $CHCl_3:CH_3OH:CH_3COOH$ (65/15/5) as solvent, autoradiographed and quantified by liquid scintillation spectrometry. Each value represents the mean ± SEM of triplicate determinations from 10 experiments.

FIGURE 14

Effect of IL-1β on ceramide-activated protein kinase activity

Cells ($30 \times 10^6$ $ml^{-1}$), handled as in FIGS. 12A and 12B, were stimulated with IL-1β (10 ng $ml^{-1}$) and homogenized at 4° C. with a Dounce homogenizer in buffer (25 mMHEPES, pH 7.4, 5 mM EGTA, 50 mM NaF and 10 μg/ml each of leupeptin and soybean trypsin inhibitor). Homogenates were centrifuged at 500×g for 5 minutes to remove nuclei and at 200,000×g for 30 minutes to prepare microsomal membranes. Membranes were resuspended into homogenizing buffer (2.2 μg membrane protein $μl^{-1}$). For assay of kinase activity, the reaction mixture contained 20 μl of microsomal membrane, 40 μl EGFR peptide (4 mg $ml^{-1}$ in 25 mM Hepes, pH 7.4) and 100 μl buffer (50 mM HEPES, pH 7.4, 20 mM $MgCl_2$) (40). Phosphorylation was initiated at 22° C. by addition of 40 μl [γ-$^{32}$P] ATP (100 μM final concentration) and terminated at the indicated times by addition of 40 μl of 0.5M ATP in 90% formic acid. Phosphorylated peptide was eluted from a $C_{18}$ Sep pak cartridge (Millipore), lyophilized, and resolved by $C_{18}$ reverse phase HPLC using a linear gradient of acetonitrile. The peptide eluted at 30% acetonitrile as determined by measuring Cerenkov radiation in 1 ml fractions. All assays were performed under conditions determined as linear for time and enzyme concentration. Enzyme activity was determined from the percent conversion of substrate to product and the specific radioactivity of [$\gamma$-$^{32}$P] ATP. Baseline kinetic analyses revealed a maximum reaction velocity of 12.5 pmol min$^{-1}$ mg$^{-1}$ of microsomal membrane protein and Michaelis constants ($K_m$) of 70 μM ATP and 0.15 mg/ml for EGFR peptide. For most studies, 100 μM ATP was used to maintain a high $^{32}$p specific radioactivity (4000 dpm pmol$^{-1}$), although qualitatively similar results were obtained with 500 μM ATP. Ceramide and sphingosine (10 nM to 1 μM) enhanced kinass activity to 1.5–2.5 of control. Values (mean ± range) represent duplicate determinations from two experiments.

FIGURES 15A AND 15B

Figure 13:
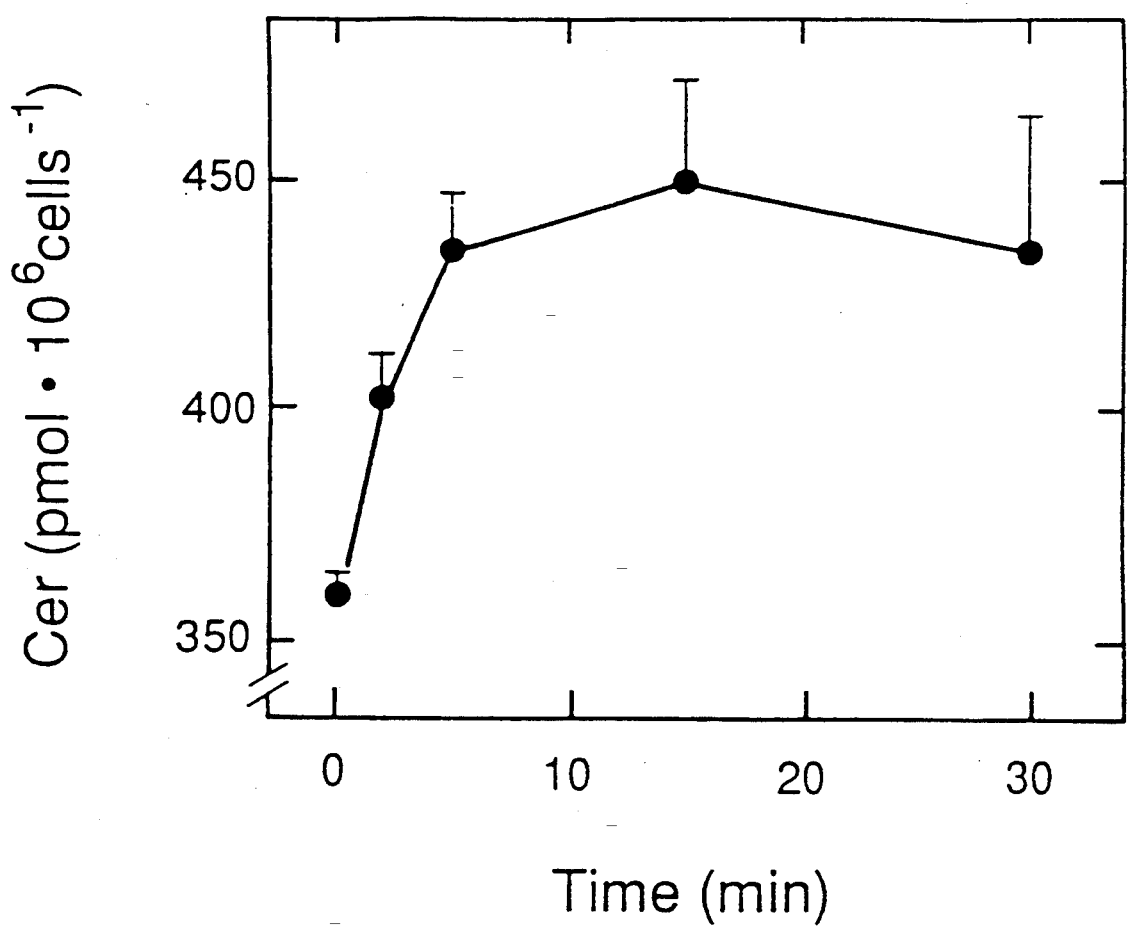
Figure 14:
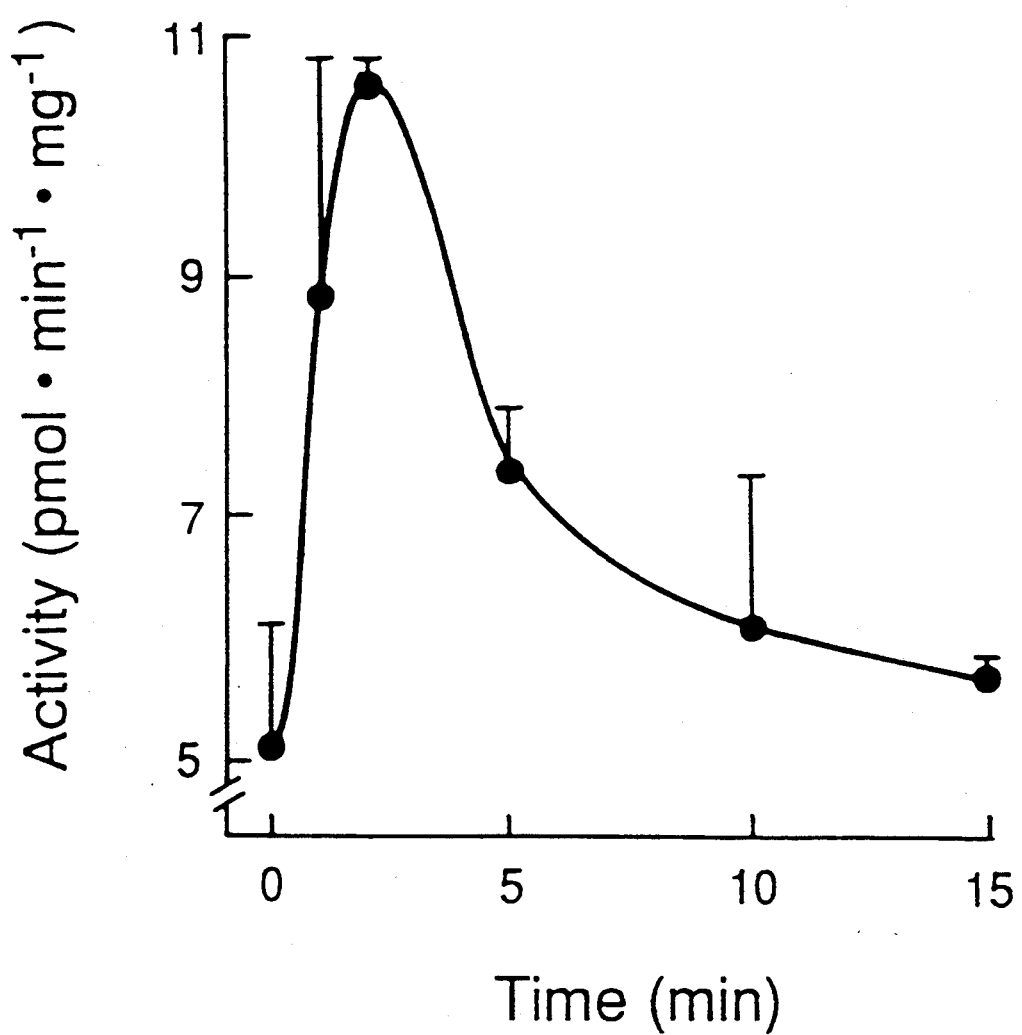

IL-1$\beta$ effects on sphingomyelin and ceramide levels (FIG. 15A) and ceramide-activated protein kinase activity (FIG. 15B) in a cell-free system Nuclei-free supernates, prepared as in FIG. 14, were incubated for 10 minutes at 4° C. with IL-1$\beta$ (10 ng ml$^{-1}$) or diluent (DME:F12 with 10% horse serum) to allow for ligand-receptor interaction. Thereafter, supernates (300 μg incubation$^{-1}$ in 25 μl ) were added to a reaction mixture (total volume 250 μl ) as described in FIG. 14. For studies measuring lipid levels, incubations were stopped by extraction of lipids into an organic phase and resolved as described in FIGS. 12A, 12B and 13. For studies measuring kinase activity, incubations contained EGFR peptide and [$^{32}$P]ATP, and phosphorylated peptide was quantified as described in FIG. 14. Background activity was subtracted from each point. Values (mean) represent data from two experiments for sphingomyelin performed in triplicate, three experiments for ceramide performed in triplicate, and five experiments for ceramide-activated protein kinase activity performed in duplicate.

DETAILED DESCRIPTION OF THE INVENTION

Specifically, the subject invention provides a purified membrane-bound ceramide-activated protein kinase having an apparent molecular weight of about 95 kD which is capable of specifically phosphorylating the threonine residue in a Pro-Leu-Thr-Pro-(SEQID NO: 1) containing polypeptide.

As used herein, "purified" means free of any other protein kinases. For example, the purified membrane-bound ceramide-activated protein kinase may include the protein kinase, membrane fragments, other non-kinase proteins, and a suitable buffer. Alternatively, the purified membrane-bound ceramide-activated protein kinase may include only the protein kinase bound by a membrane and a suitable buffer.

By way of example, the membrane-bound ceramide-activated protein kinase of the subject invention may be purified by (a) solubilizing the protein kinase from the membrane, (b) separating the protein kinase from strong anions, and from protein kinase C and MAP kinases by DE52 anion exchange chromatography, (c) performing preparative SDS-gel electrophoresis based on conditions determined from a denaturation/renaturation reaction, (d) performing a high resolution isoelectric focussing using a Rotofor apparatus, (e) performing strong anion exchange chromatography by HPLC, (f) performing hydrophobic column chromatography by HPLC, and (g) performing continuous elution electrophoresis, thereby purifying the protein kinase. The purified protein kinase may then be affixed to a membrane for proper kinase function.

As used herein, "ceramide-activated" means having activity which is accelerated by the presence of ceramide. Specifically, the protein kinase of the subject invention is capable of phosphorylating certain protein substrates (e.g. human epidermal growth factor receptor) if the kinase is membrane-bound, and is in the presence of $Mg^{+2}$ and ATP. However, the rate at which the protein kinase phosphorylates its protein substrate is increased by the presence of ceramide.

The purified protein kinase of the subject invention comprises a single peptide chain having an apparent molecular weight of approximately 95 kD. The molecular weight was determined using a denaturation/renaturation procedure well known to those skilled in the art. Briefly, the method involves running the protein of interest on a denaturing gel having substrate embedded therein, washing the gel, allowing the protein to renature, assaying for protein activity in situ thereby locating the protein on the gel, and comparing the location of the protein on the gel with that of molecular weight markers, thereby determining the molecular weight of the protein.

As used herein, "specifically phosphorylating" means phosphorylating the threonine residue in a Pro-Leu-Thr-Pro-(SEQID NO: 1) containing polypeptide without phosphorylating other amino acid residues which ordinarily serve as phosphate acceptors (e.g. serine and tyrosine).

As used herein, "polypeptide" means a single chain of amino acid residues. Accordingly, a Pro-Leu-Thr-Pro-(SEQID NO: 1) containing polypeptide may be the polypeptide Pro-Leu-Thr-Pro (SEQID NO: 1) or a larger peptide containing this amino acid sequence.

The subject invention also provides a method of determining whether an agent is capable of specifically inhibiting the phosphorylation activity of the ceramide-activated protein kinase of the subject invention which comprises: (a) contacting the protein kinase with a predetermined amount of a polypeptide containing the amino acid sequence Pro-Leu-Thr-Pro(SEQID NO: 1), and the agent, under conditions i) which would permit activity of the protein kinase to be linear with respect to time and protein kinase concentration in the absence of the agent, and ii) which would permit the specific phosphorylation by the protein kinase of a predetermined number of the threonine residues in such predetermined amount of the Pro-Leu-Thr-Pro-(SEQID NO: 1) containing polypeptide in the absence of the agent; (b) quantitatively determining the percentage of such predetermined number of threonine residues which are specifically phosphorylated in the presence of the agent, thereby determining whether the agent is capable of inhibiting the activity of the ceramide-activated protein kinase; and (c) determining whether the agent inhibits the activity of a non-ceramide-activated kinase, so as to determine whether the agent is capable of specifically inhibiting the activity of the ceramide-activated protein kinase.

As used herein, the term "agent" includes both protein and non-protein moieties. For example, the agent may be a ceramide analog or an antibody directed against a portion of the ceramide-activated protein kinase of the subject invention.

As used herein, "capable of specifically inhibiting" means capable of reducing the phosphorylation activity of the ceramide-activated protein kinase of the subject invention by at least two-fold, but not capable of reducing the phosphorylation activity of a non-ceramide-activated protein kinase. As used herein, a "non-ceramide-activated protein kinase" is a protein kinase whose phosphorylation activity is not altered in the presence of ceramide. An example of a non-ceramide-activated protein kinase is protein kinase C.

As used herein, "phosphorylation activity" means the rate at which a protein kinase phosphorylates its substrate. Accordingly, the phosphorylation activity of the ceramide-activated protein kinase of the subject invention means the rate at which the protein kinase phosphorylates the threonine residue in a Pro-Leu-Thr-Pro-(SEQID NO: 1) containing polypeptide substrate.

As used herein, conditions which would permit activity of the protein kinase to be linear with respect to time and protein kinase concentration in the absence of the agent are simply conditions in which Michaelis-Menten enzyme kinetics are observed. Specifically, Michaelis-Menten enzyme kinetics are observed when the enzyme concentration is low in comparison with that of the substrate, i.e. the enzyme concentration is rate-limiting, and the enzyme reaction has not yet approached completion.

Quantitatively determining the number of threonine residues which are specifically phosphorylated may be achieved by measuring the kinase reaction rate while Michaelis-Menten kinetics are observed, and from the rate measurement, calculating the number of threonine residues which are specifically phosphorylated. Such methods of calculation are well known to those skilled in the art.

An example of the method of the subject invention is provided infra. A rate-limiting amount of membrane-bound ceramide-activated protein kinase is contacted with X μg of polypeptide containing the amino acid sequence Pro(SEQID NO: 1)-Leu-Thr-Pro(SEQID NO: 1), and having Y moles of threonine residues in the Pro-Leu-Thr-Pro sequence, together with an agent under conditions which would permit the phosphorylation of $0.1 \times Y$ moles of threonine residues in the absence of the agent. In the presence of the agent, $0.05 \times Y$ moles of threonine residues are phosphorylated. The agent is shown not to inhibit protein kinase C (a non-ceramide-activated protein kinase) activity using a histone III$_S$ substrate assay well known to those skilled in the art. Accordingly, the agent specifically inhibits the activity of the ceramide-activated protein kinase.

In one embodiment of the subject invention, the polypeptide containing the amino acid sequence Pro-Leu-Thr-Pro (SEQID NO: 1) is human epidermal growth factor receptor.

The subject invention further provides a method of determining whether an agent is capable of specifically stimulating the phosphorylation activity of the ceramide-activated protein kinase of the subject invention which comprises: (a) contacting the protein kinase with a predetermined amount of a polypeptide containing the amino acid sequence Pro-Leu-Thr-Pro(SEQID NO: 1), and the agent, under conditions i) which would permit activity of the protein kinase to be linear with respect to time and protein kinase concentration in the absence of the agent, and ii) which would permit the specific phosphorylation by the protein kinase of a predetermined number of the threonine residues in such predetermined amount of the Pro-Leu-Thr-Pro-(SEQID NO: 1) containing polypeptide in the absence of the agent; (b) quantitatively determining the percentage of such predetermined number of threonine residues which are specifically phosphorylated in the presence of the agent, thereby determining whether the agent is capable of stimulating the activity of the ceramide-activated protein kinase; and (c) determining whether the agent stimulates the activity of a non-ceramide-activated kinase, so as to determine whether the agent is capable of specifically stimulating the activity of the ceramide-activated protein kinase.

As used herein, the term "agent" includes both protein and non-protein moieties. For example, the agent may be a ceramide analog, an antibody directed against a portion of the ceramide-activated protein kinase of the subject invention, tissue necrosis factor e or interleukin I.

As used herein, "capable of specifically stimulating" means capable of increasing the phosphorylation activity of the ceramide-activated protein kinase of the subject invention by at least two-fold, but not capable of increasing the phosphorylation activity of a non-ceramide-activated protein kinase.

In one embodiment of the subject invention, the polypeptide containing the amino acid sequence Pro-Leu-Thr-Pro (SEQID NO: 1) is human epidermal growth factor receptor.

An example of the method of the subject invention is provided infra. A rate-limiting amount of membrane-bound ceramide-activated protein kinase is contacted with X μg of polypeptide containing the amino acid sequence Pro-Leu-Thr-Pro(SEQID NO: 1), and having Y moles of threonine residues in the Pro-Leu-Thr-Pro (SEQID NO: 1)sequence, together with an agent under conditions which would permit the phosphorylation of $0.1 \times Y$ moles of threonine residues in the absence of the agent. In the presence of the agent, $0.2 \times Y$ moles of threonine residues are phosphorylated. The agent is shown not to stimulate protein kinase C (a non-ceramide-activated protein kinase) activity using a histone III$_S$ substrate assay well known to those skilled in the art. Accordingly, the agent specifically stimulates the activity of the ceramide-activated protein kinase.

The subject invention further provides a method of treating a subject having an inflammatory disorder which comprises administering to the subject an agent capable of inhibiting the phosphorylation activity of a ceramide-activated protein kinase of T helper cells and macrophage cells of the subject in an amount effective to inhibit said phosphorylation activity, thereby reducing the inflammation associated with the disorder.

In the preferred embodiment of the subject invention, the subject is a human. The inflammatory disorder may be rheumatoid arthritis, ulcerative colitis, graft versus host disease, lupus erythematosus or septic shock.

In the practice of the subject invention, the administering of the agent may be effected or performed using any of the various methods known to those of skill in the art. For example, the administration may comprise administering intravenously, intramuscularly or subcutaneously.

Further in the practice of the subject invention, the amount of agent effective to inhibit the phosphorylation activity of ceramide-activated protein kinase of T helper cells and macrophage cells of the subject means an amount capable of inhibiting the phosphorylation activity by at least two-fold. This amount may be calculated using any of the various methods known to those of skill in the art.

The subject invention further provides a method of treating a human subject infected with HIV so as to reduce the proliferation of HIV in the human subject which comprises administering to the human subject an agent capable of inhibiting the phosphorylation activity of a ceramide-activated protein kinass of HIV-infected cells of the human subject in an amount effective to inhibit said activity, thereby reducing the proliferation of HIV in the human subject.

In the practice of the subject invention, the administering of the agent may be effected or performed using any of the various methods known to those of skill in the art. For example, the administration may comprise administering intravenously, intramuscularly or subcutaneously.

Further in the practice of the subject invention, the amount of agent effective to inhibit the phosphorylation activity of ceramide-activated protein kinass of the HIV-infected cells of the human subject may be calculated using any of the various methods known to those of skill in the art.

The subject invention further provides a method of determining whether a human subject is infected with HIV which comprises obtaining a sample of cells from the human subject, said cells being susceptible to infection by HIV, contacting the sample of cells with an agent capable of stimulating the phosphorylation activity of a ceramide-activated protein kinass of the cells of the sample in an amount effective to stimulate said phosphorylation activity and thereby stimulating the proliferation of any HIV present in the cells, detecting in the resulting sample the presence of any HIV, the presence of HIV indicating that the human subject is infected with HIV.

As used herein, the "sample" may be obtained from blood or any other bodily fluid known to contain HIV in HIV-infected individuals. The agent capable of stimulating the phosphorylation activity of a ceramide-activated protein kinase may be interleukin-I.

As used herein, detecting the presence of HIV may be performed according to any of the various methods known to those skilled in the art. Such methods include, but are in no way limited to, immunoassays against the coat proteins.

Further in the practice of the subject invention, the amount of agent effective to stimulate the phosphorylation activity of ceramide-activated protein kinase of the cells of the sample means an amount capable of stimulating the phosphorylation activity by at least two-fold. This amount may be calculated using any of the various methods known to those of skill in the art.

Finally, the subject invention provides a method of treating a subject having a disorder associated with poor stem cell growth, which comprises administering to the subject an agent capable of stimulating the phosphorylation activity of a ceramide-activated protein kinase of the stem cells of the subject in an amount effective to stimulate said phosphorylation activity, thereby stimulating stem cell growth.

In the preferred embodiment of the subject invention, the subject is a human. Also, in the preferred embodiment of the subject invention, the disorder associated with poor stem cell growth is aplastic anemia.

In one embodiment of the subject invention, the agent is interleukin-I. The interleukin-I may be interleukin-I$\beta$.

Further in the practice of the subject invention, the amount of agent effective to stimulate the phosphorylation activity of ceramide-activated protein kinase of the stem cells of the subject means an amount capable of stimulating the phosphorylation activity by at least two-fold. This amount may be calculated using any of the various methods known to those of skill in the art.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

I - Characterization of a ceramide-activated protein kinase: Stimulation by tumor necrosis factor $\alpha$ A. Abstract Recent investigations have identified a signal-transduction system involving sphingomyelin and derivatives. In this paradigm, sphingomyelin hydrolysis by a sphingomyelinase generates ceramide, which may be converted to the protein kinase C inhibitor sphingosine or to ceramide 1-phosphate. Ceramide may have second-messenger function because it induces epidermal growth factor receptor phosphorylation, presumably on Thr-669 in A-431 cells. The present study describes a kinase that may mediate ceramide action. With a 19-amino acid epidermal growth factor receptor peptide containing Thr-669, a membrane-bound activity that phosphorylated the peptide was detected in A-431 cells. Activity was inearly related to ATP (0.3–300$\mu$M) and peptide concentration (0.02–1 mg/ml), possessed a physiologic pH optimum (pH 7.0–7.4), and was $Mg^{2+}$-dependent. Other cations—$Ca^{2+}$, $Mn^{2+}$, and $Zn^{2+}$—were ineffective. Natural and synthetic ceramide induced time-and concentration-dependent enhancement of kinase activity. Ceramide (0.5 $\mu$M) increased kinase activity 2-fold by 30 s, and activity remained elevated for at least 15 minutes. As little as 0.001 $\mu$M ceramide was effective, and 1 $\mu$M ceramide induced maximal phosphorylation. Sphingosine was similarly effective. Because tumor necrosis factor (TNF) e rapidly induces sphingomyelin hydrolysis to ceramide during monocytic differentiation of HL-60 cells, its effects on kinase activity were assessed. Kinase activity was increased 1.5-fold at 5 minutes and 2-fold at 2 hr in membranes derived from TNF-stimulated cells. The effective concentration range was 3 pM-30 nM TNF. Exogenous ceramide induced a similar effect. In sum, these studies demonstrate the existence of an unusual $Mg^{2+}$-dependent ceramide-activated protein kinase that may mediate some aspects of TNF-$\alpha$ function.

B. Background

The present studies were done to identify the kinase that mediated the effect of ceramide on EGFR phosphorylation. The substrate used was a synthetic peptide derived from the amino acid sequence around Thr-669 of the EGFR. These studies demonstrate that A-431 human epidermoid carcinoma cells and HL-60 cells contain a ceramide/sphingosine-activated protein kinase. Further, this kinase is stimulated by TNF-$\alpha$, which elevates the cellular ceramide level and induces phosphorylation of several proteins (19–24), including the EGFR, as an early event in cellular activation.

These studies provide initial evidence for a sphingolipid-activated, protein kinase-mediated signaling system.

C. Experimental Procedures

1. Materials

Ceramide (type III), sphingosine, palmitic acid, cholera toxin, hexamethylene bisacetamide, retinoic acid, butyrate, leupeptin, and buffers were from Sigma. Fetal bovine serum (FBS) was from GIBCO. [$\gamma$-$^{32}$P] ATP (3000 Ci/mmol; 1 Ci=37 GBq) was from New England Nuclear. P81 phosphocellulose paper was from Whatman. Liquid scintillation solution (Liquiscint) was from National Diagnostics (Sommerville, N.J.). HPLC grade solvents were from Fisher. The EGFR peptide (amino acids 663–681, NH$_2$-Glu-Leu-Val-Glu-Pro-Leu-Thr-Pro-Ser-Gly-Glu-Ala-Pro-Asn-Gln-Ala-Leu-Leu-Arg-COOH(SEQ ID NO: 2) was synthesized by using an Applied Biosystems model 431A machine and purified by reverse-phase HPLC. C$_8$-ceramide (N-octanoylsphingosine; C$_8$-cer) and TNF $\alpha$ may be prepared according to methods well known to those of skill in the art. TNF$\alpha$ is also commercially available.

2. Cell Culture

A-431 human epidermoid carcinoma cells were grown in monolayer culture in a 1:1 mixture of Dulbecco's modified Eagle's medium (DMEM) and Ham's F-12 medium containing 10% FBS and were harvested by trypsinization according to methods well knownto those skilled in the art (18). HL-60 cells were grown in suspension culture in RPMI 1640 medium containing 10% FBS and supplements, according to methods well known to those skilled in the art (3). On the day of an experiment HL-60 cells were resuspended ($1 \times 10^6$ cells per ml) in RPMI 1640 medium/1% FBS for 2 hours before stimulation with lipid activators and differentiating agents.

3. Membrane Preparation

Cells ($3 \times 10^7$/ml) were homogenized with a tight-fitting Dounce homogenizer at 4° C. in buffer (25 mM Hepes, pH 7.4/5 mM EGTA/50 mM NaF/leupeptin at 10 $\mu$g/ml) according to methods well known to those skilled in the art (17). The homogenate was centrifuged at 500$\times$g for 5 minutes, and the postnuclear supernatant was centrifuged at 200,000$\times$g for 30 minutes. The microsomal membrane pellet was resuspended (7.5 $\mu$g of membrane protein per $\mu$l for A-431 cells and 1.5 $\mu$g/$\mu$l for HL-60 cells) in homogenizing buffer. Membranes were prepared fresh daily.

4. Assay of Kinase Activity

For most experiments, the reaction mixture contained 25 $\mu$l of microsomal membrane or postnuclear supernatant, 50 $\mu$l of EGFR peptide (4 mg/ml in 25 mM Hepes, pH 7.4) and 125 $\mu$l of buffer (50 mMHepes, pH 7.4/20 mMMgCl$_2$) (17). Phosphorylation was initiated at 22° C. by addition of 50 $\mu$l of [$\gamma$-$^{32}$P] ATP (150 $\mu$M final concentration; 4000 dpm/pmol). For studies with lipid activators, ceramide and other lipids were dried under N$_2$ and resuspended in the kinase assay buffer by bath sonication for 2 minutes at 37° C. The reaction was terminated at the indicated times by addition of 50 $\mu$l of 0.5M ATP in 90% formic acid. Unless otherwise indicated, all assays were done under conditions determined as linear for time and enzyme concentration. Enzyme activity was determined from the transfer of $^{32}$P from the $\gamma$ position of ATP to EGFR peptide and the specific radioactivity of [$\gamma$-$^{32}$P] ATP.

Phosphorylated peptide was quantified by two separate methods. For initial studies, samples were spotted on phosphocellulose paper, washed in 1M acetic acid/4 mM pyrophosphate and subjected to liquid scintillation counting, according to methods well known to those skilled in the art (25). Values obtained from a boiled blank or a sample lacking peptide were subtracted from each determination. Alternatively, HPLC was done according to methods well known to those skilled in the art (17). For these studies, samples were first applied to a C$_{18}$ Sep-Pak cartridge and eluted With 99.9% acetonitrile/0.1% trifluoroacetic acid. The eluates were lyophilized, resuspended in 6M guanidine hydrochloride/200 mM Tris, pH 8.5 and applied to a C$_{18}$ reverse-phase column (Dynamax, 4.6 mm i.d., Rainin, Woburn, Mass.). The peptide was eluted with a linear gradient (1% per minute) of acetonitrile at a flow rate of 1 ml/minute and was detected by measuring the Cerenkov radiation associated with 1-ml fractions.

5. Phosphoamino Acid Analysis

To determine which amino acid was phosphorylated, phosphoamino acid analysis of the peptide was done. The phosphopeptide peak obtained by HPLC was subjected to partial acid hydrolysis (1 hr at 110° C. in 6M HCl). The hydrolysates were dried, resuspended in 250 $\mu$l of water, and applied to a Dowex AG1-X8 column (Bio-Rad). Amino acids were eluted with 0.5M HCl, dried, and analyzed by thin-layer electrophoresis, according to methods well known to those skilled in the art (26). Individual phosphoamino acids were identified by ninhydrin staining of carrier phosphoamino acids and by autoradiography.

6. Other Procedures

Protein was measured by the method of Bradford (27).

7. Statistics

Statistical analysis was performed by t test and linear regression analysis by the method of least squares.

D. Results

Davis and coworkers (15, 17) showed that addition of sphingosine to A-431 cells enhanced phosphorylation of the EGFR on Thr-669. Subsequently, the subject experiments show that sphingosine was rapidly converted to ceramide in these cells and that exogenous ceramide induced identical effects (18). To investigate the kinase that mediated ceramide action, a synthetic peptide corresponding to the sequence around Thr-669 was used as substrate.

Initial studies were done to determine the kinetics of phosphorylation of the EGFR peptide. The conditions for this assay were adapted from Davis and coworkers (17, 25). Briefly, postnuclear supernatant was used as a source of enzyme activity, and samples were spotted on phosphocellulose paper to measure phosphorylated peptide. The kinetics of phosphorylation appeared biphasic. Initial rapid incorporation of $^{32}$p into peptide for 10 minutes was followed by incorporation at a slightly reduced rate for as long as 30 minutes (FIG. 1).

Subsequent studies were done to optimize the assay. Kinase activity was found by Lineweaver-Burke analysis to be linearly related ($r = 0.98$) to substrate concentration for ATP (0.3–300$\mu$M) and EGFR peptide (0.02–1 mg/ml) at 5 minutes of stimulation. Apparent K$_m$ values for ATP of 15 $\mu$M and for EGFR peptide of 0.25 mg/ml were derived. Apparent V$_{max}$ values ranged from 100–200 pmol.min$^{-1}$/mg of protein$^{-1}$. All subsequent studies were done with 150 $\mu$M ATP and EGFR peptide at 4 mg/ml. Under these conditions, substrate concentration was not rate limiting.

An additional set of studies assessed the pH optimum for the kinase activity. There was no measurable activity at pH values <5. Thereafter, peptide phosphorylation increased to a maximum at pH 7-7.4 and rapidly dropped to undetectable levels at pH 8. Hence, this kinase appears active within the physiologic pH range.

The divalent cation requirement for kinase activity was also investigated. In the presence of EGTA (1 mM) alone, peptide phosphorylation did not occur. $Mg^{2+}$ induced dose-dependent peptide phosphorylation (FIG. 2). As little as 0.1 mM $Mg^{2+}$ increased kinase activity to 4 pmol.min$^{-1}$ (mg of protein$^{-1}$), and maximal activity occurred with 10 mM $Mg^{2+}$; the $ED_{50}$ was $\approx$3.5 mM. An increase in $Mg^{2+}$ to 25 mM did not further increase activity. $Mn^{2+}$ (1-10 mM), $Zn^{2+}$ (1-10 mM), and $Ca^{2+}$ (0.001-10mM) did not support kinase activity toward the EGFR peptide. These studies indicate that this kinase activity is $Mg2+$-dependent.

Cell-fractionation studies were done to compare levels of kinase activity in the postnuclear supernatant, cytosol, and membrane. Activity detected in the postnuclear supernatant was equally divided between membrane and cytosolic fractions. Only membrane activity was enhanced by ceramide (see below).

Figure 3:
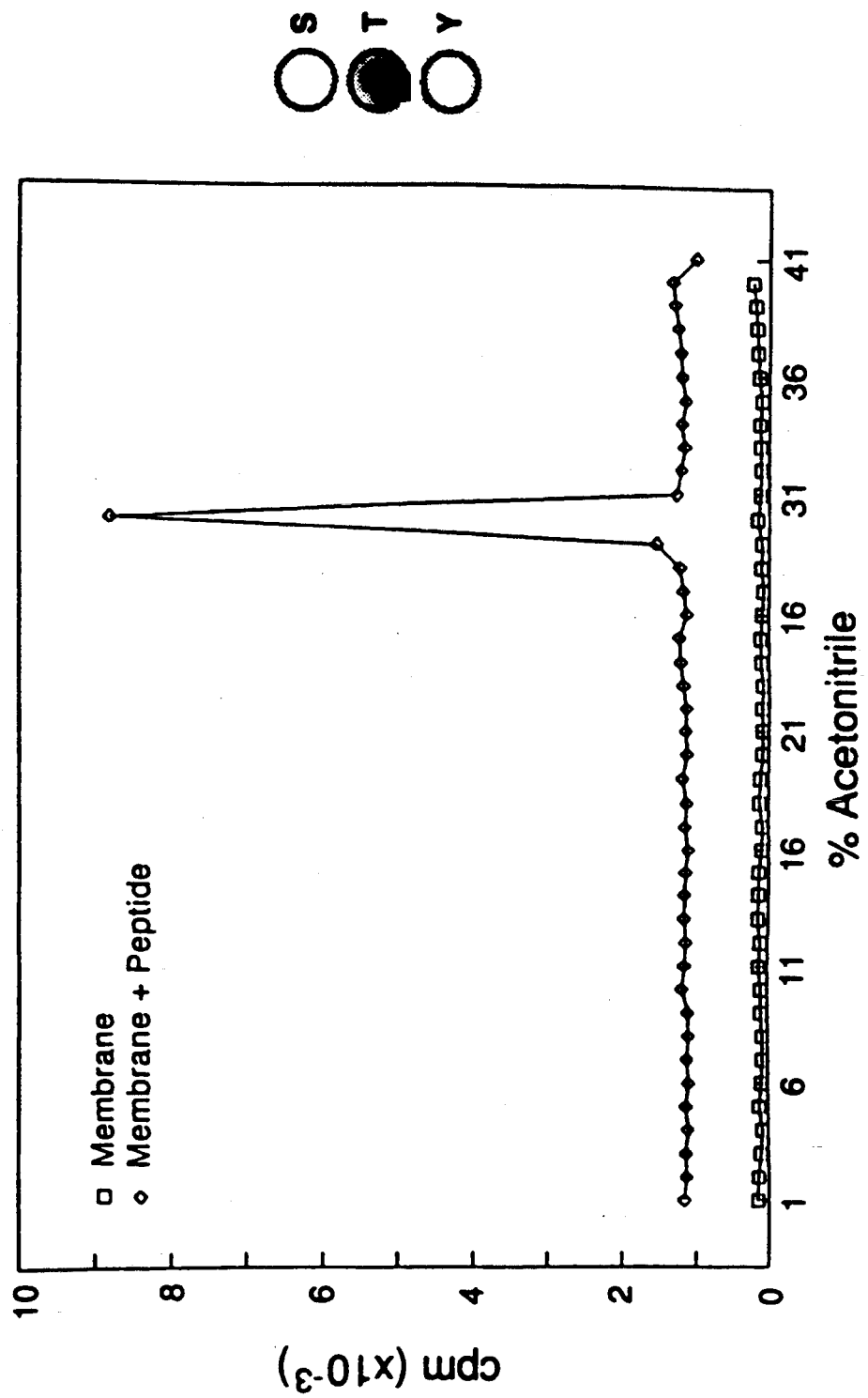

A more specific method for detection of phosphorylated peptide used reverse-phase HPLC. Peptide was eluted with a linear gradient of acetonitrile, and fractions were monitored for Cerenkov radiation. A peak of Cerenkov radiation was eluted at 30% acetonitrile in samples containing peptide but was absent when the peptide was omitted from the reaction mixture (FIG. 3, Left). Phosphoamino acid analysis of the eluate demonstrated the presence of [$^{32}$P] phosphothreonine (FIG. 3, Right).

These studies indicate that of the two potential phosphorylation sites contained within the EGFR peptide, corresponding to Thr-669 and Ser-671, only threonine-669 served as substrate.

Figure 4:
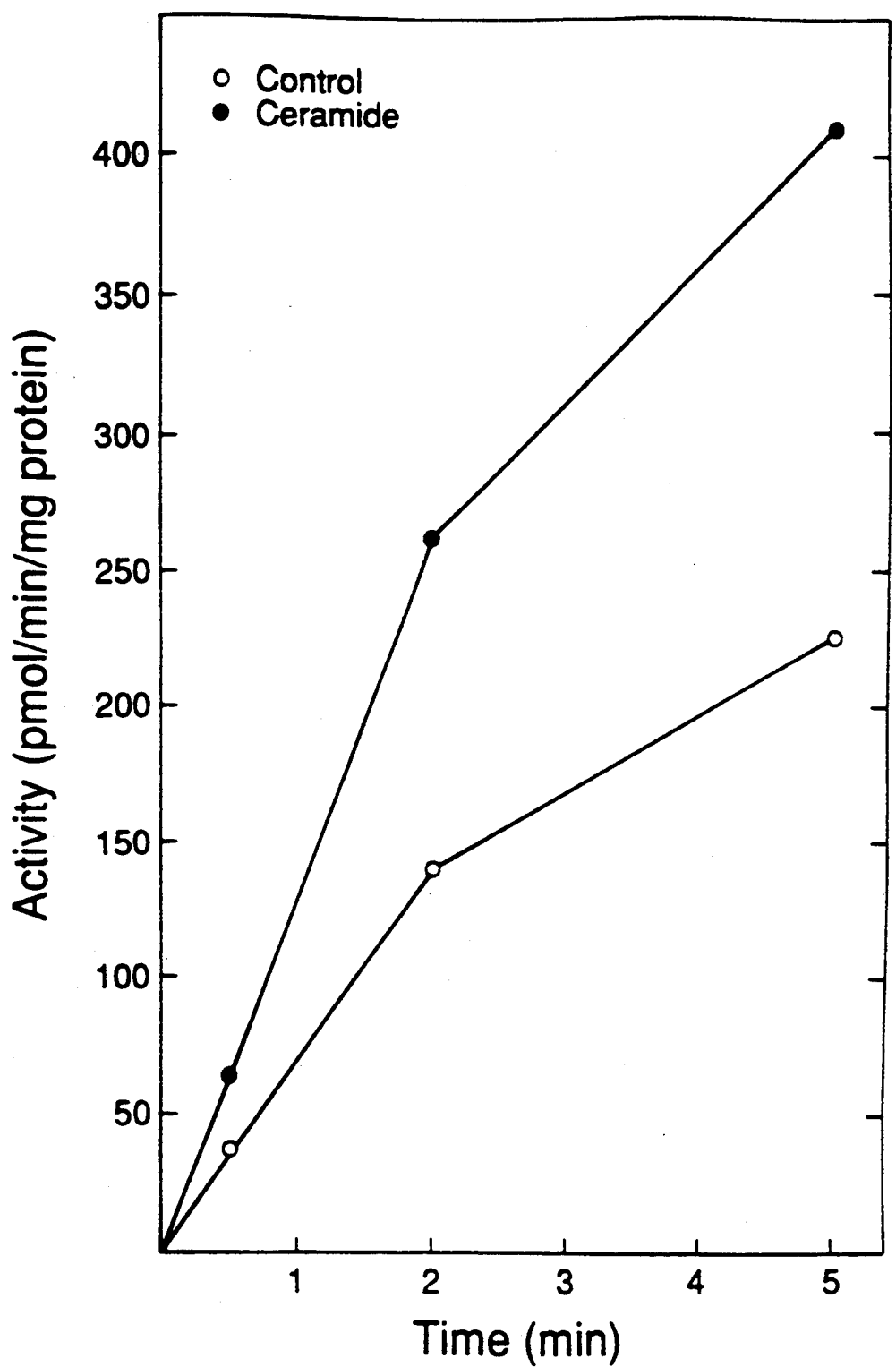

To determine whether ceramide and sphingosine enhance EGFR peptide phosphorylation, these lipids were added to a reaction mixture containing peptide and membrane. Ceramide (0.5 $\mu$M) stimulation of EGFR peptide phosphorylation was evident by 30 s (FIG. 4) and demonstratable for at least 15 minutes. Ceramide (0.001-3$\mu$M) enhanced peptide phosphorylation in a concentration-dependent manner at 2 minutes of stimulation (FIG. 5). As little as 1 nM ceramide was effective, and a maximal effect to 2.1-fold of control occurred with 1 $\mu$M ceramide; the $ED_{50}$ was $\approx$30 nM. Synthetic $C_8$-cer and natural ceramide (Sigma type III) were similarly effective. As with basal phosphorylation, ceramide-enhanced phosphorylation occurred exclusively on the threonine residue of the EGFR peptide.

Figure 6:
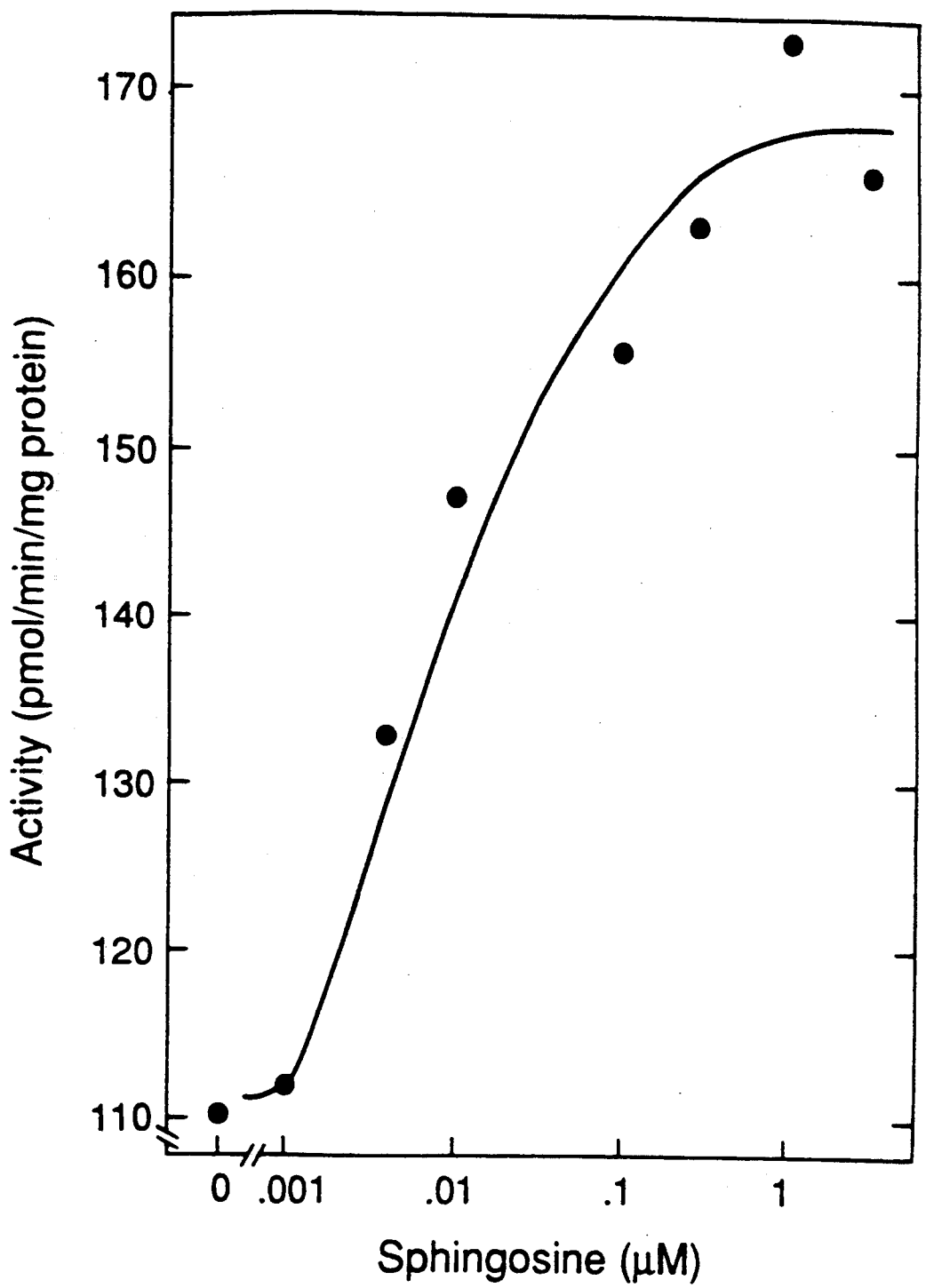

FIG. 6 shows that sphingosine also stimulated EGFR peptide phosphorylation to a level 1.6 fold of control at 2 minutes of stimulation. The concentration-dependence of this stimulatory effect was similar to that of ceramide. In contrast, palmitic acid, the predominant fatty acid in natural ceramide, failed to increase EGFR peptide phosphorylation.

Figure 8:
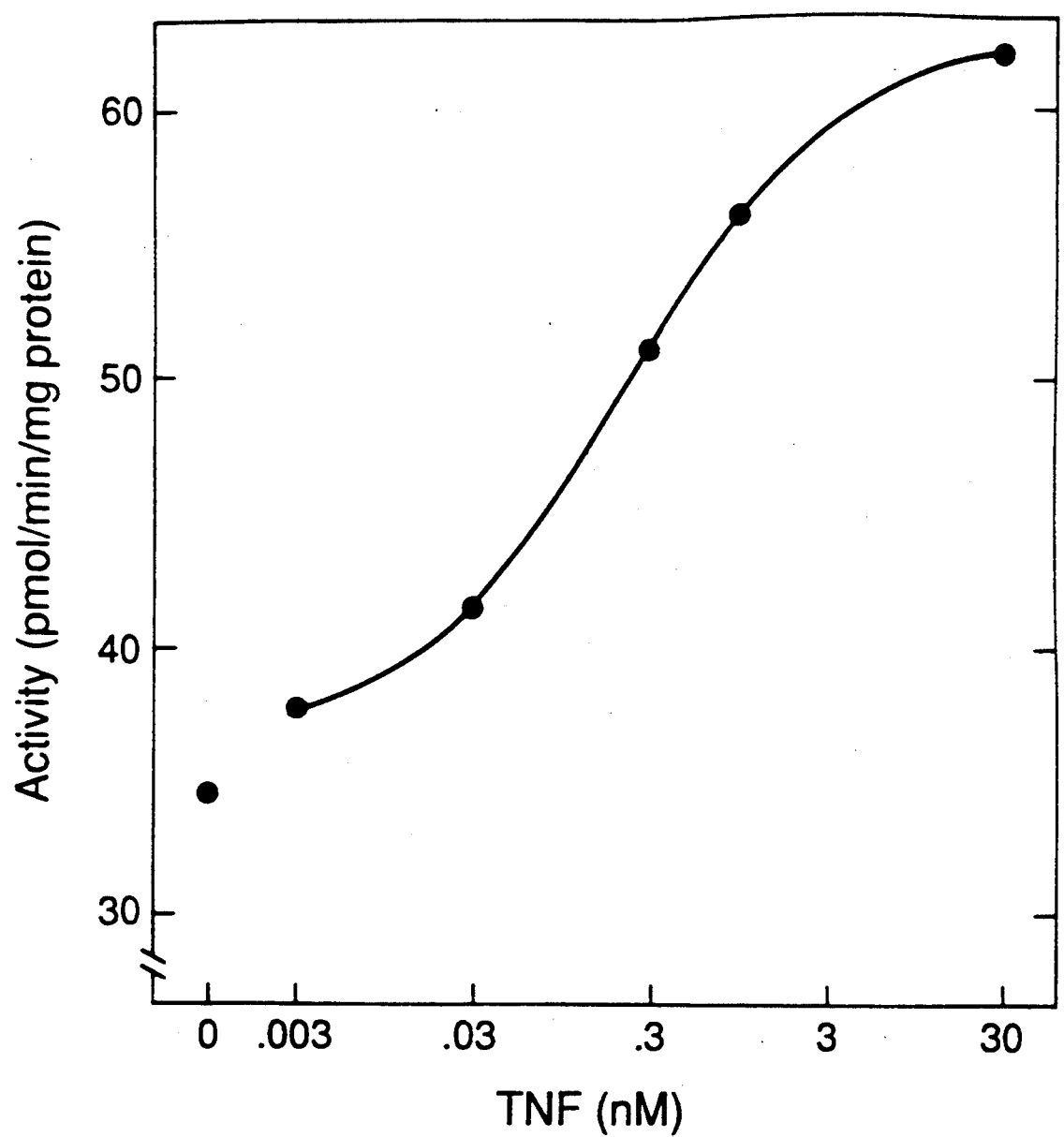

TNF-$\alpha$ has been shown to increase cellular levels of ceramide within minutes of activation of HL-60 cells, and a synthetic ceramide replaced the requirement of TNF-$\alpha$ in monocytic differentiation of these cells (6). Hence, studies were done to determine whether TNF-$\alpha$ treatment of HL-60 cells activated a kinase similar to that detected in A-431 cells. For these studies, cells were stimulated with TNF-$\alpha$, and then membranes were isolated and used to assess kinase activity toward the EGFR peptide. FIG. 7 demonstrates kinetics of the effect of 30 nM TNF-$\alpha$, a maximally effective concentration for generation of ceramide and monocyte differentiation of these cells (6). Cellular stimulation for as little as 5 minutes increased membrane-bound kinase activity to 1.5-fold of control, and activity continued to increase for as long as 2 hours to 2.2-fold of control. The effect of TNF-$\alpha$ was concentration-dependent when measured at 60 minutes of stimulation (FIG. 8). As little as 3 pM TNF-$\alpha$ increased activity to 1.1-fold of control, and a maximal effect of 1.8-fold of control occurred with 30 nM TNF-$\alpha$; the $ED_{50}$ was $\approx$200 pM. Additional studies assessed the effect of the cell-permeable synthetic ceramide, $C_8$-cer, on enzyme activity. In three separate studies, addition of as little as 0.3 $\mu$M $C_8$-cer to the medium of HL-60 cells increased kinase activity in membranes derived from stimulated cells to 1.2-fold of control, and a maximal effect was achieved with 10 $\mu$M $C_8$-cer to 1.5-fold of control. This value was quantitatively similar to that obtained with a maximal concentration of TNF-$\alpha$ in this set of studies. Sphingosine was similarly as effective as C8-cer. Kinase activity was not stimulated by maximally effective concentrations of other HL-60 differentiating agents, including cholera toxin (10 nM), retinoic acid (0.5 $\mu$M), and butyrate (0.5 mM) (28, 29). In sum, these studies demonstrate that HL-60 cells, like A-431 cells, contain a ceramide-activated protein kinase and that TNF-$\alpha$, which generates ceramide as an early event in cellular activation, enhances kinase activity.

E. Discussion

Davis et al. (15, 17) originally demonstrated that sphingosine stimulated phosphorylation of the EGFR on Thr-669 in A-431 cells. It is shown here that sphingosine was rapidly converted to ceramide in these cells and that ceramide induced identical effects. To investigate the kinase that mediated ceramide action, the present studies used a 19-amino acid synthetic peptide corresponding to the sequence around Thr-669 of the EGFR as a substrate. These studies have demonstrated that A-431 cells contain a $Mg^{2+}$-dependent kinase activity with a physiologic pH optimum that was stimulated by ceramide in a time- and concentration-dependent manner. This kinase has some distinctive features. It appears exclusively membrane-bound, does not utilize $Ca^{2+}$ as cofactor, and is also activated by the protein kinase C inhibitor sphingosine. These features distinguish this kinase from any other known protein kinase. A similar activity was detected in HL-60 cells and was enhanced rapidly by TNF-$\alpha$, which elevates ceramide (but not sphingosine) levels, as an early event in cellular activation.

Several studies have demonstrated that TNF-$\alpha$ stimulates protein phosphorylation as a proximal event in cellular stimulation (19-24). A variety of substrates have been identified, including a 28-kDa stress protein in bovine aortic endothelial cells (21), the eukaryotic initiation factor 4E (22, 23), an uncharacterized 26-kDa cytosolic protein in U937 human monoblastoid cells (20), and the EGFR (24). In most of these studies serine/threonine phosphorylation of these proteins was seen, and different investigators have suggested that the cAMP-dependent protein kinase (30), protein kinase C (31, 32), or some other protein kinase mediates TNF action (33). The present studies strongly suggest that another serine/threonine protein kinase, in some systems, mediates TNF action.

The amino acid sequence surrounding Thr-669 of the EGFR is unusual, containing three proline residues within a span of 9 amino acids. This unusual structure has no homology to the consensus substrate sequences for any of the major protein kinases (34, 35). In fact, Gill and coworkers (36) reported that a peptide corresponding to residues 662–673 of the EGFR failed to serve as substrate for a variety of purified protein kinases in vitro, including the cAMP-dependent protein kinase, protein kinase C, calcium-calmodulin-dependent protein kinase, and S6 kinase. Only casein kinase II and glycogen synthase kinase 3 demonstrated significant activity toward this substrate, but the peptide proved to be a poor substrate for both of these kinases, as evidenced by high Km values. Glycogen synthase kinase 3 has a known preference for proline-rich substrates, which may account for the low level of activity detected in these studies (37).

The region corresponding to Thr-669 of the EGFR is located between the transmembrane domain and the ATP-binding site within the catalytic domain. This region also contains Thr-654, the major protein kinase C phosphorylation site, and the region, in general, is considered to be involved in modulation of receptor function (38). Mutational removal of Thr-669 has been shown to alter receptor down-regulation and substrate specificity (36). This region is also highly conserved in the v-erbB and neu oncogene products and may represent a site for phosphorylation of these proteins by ceramide-activated protein kinase.

In sum, these studies characterize a ceramide-activated protein kinase activity in A-431 and HL-60 cells. Evidence has been presented that this kinase is activated by TNF-α, which triggers the generation of ceramide as an early event during cellular stimulation. Hence, this kinase may mediate, in whole or in part, signal transduction by TNF-α in some systems. In this paradigm, binding of TNFα to its cell-surface receptor stimulates a neutral plasma membrane-bound sphingomyelinase that cleaves sphingomyelin to yield ceramide. Ceramide would then enhance kinase activity, resulting in the phosphorylation of specific substrates.

II - Tumor Negrosis Factor-α Activates the Sphingomyelin Signal Transduction Pathway in a Cell-Free System A. Abstract The mechanism of tumor necrosis factor (TNF)-α signaling is unknown, however, TNF-α signaling most likely involves sphingomyelin hydrolysis to ceramide by a sphingomyelinase and stimulation of a ceramide-activated protein kinass. In a cell-free system, TNF-α induced a rapid reduction in membrane sphingomyelin content and a quantitative elevation in ceramide concentrations. Ceramide-activated protein kinase activity also increased. Kinass activation was mimicked by addition of sphingomyelinase but not by phospholipases $A_2$, C, or D. Reconstitution of this cascade in a cell-free system demonstrates tight coupling to the receptor, suggesting that this is a signal transduction pathway for TNF-α.

B. Experimental Procedure and Discussion

Sphingomyelin can be metabolized to generate molecules that have various functions within the cell (1–6). Ceramide, which is generated by sphingomyelinase action, can be deacylated to sphingoid bases (1, 14), which are potential inhibitors of protein kinase C (9–11) or phosphorylated to ceramide 1-phosphate (4) by a ceramide kinase (5, 13). Ceramide appears to have bioeffector properties (7, 8, 18). Cell-permeable ceramide analogs stimulate monocytic differentiation of human leukemia (HL-60) cells (7, 8) and the phosphorylation of the epidermal growth factor receptor (EGFR) at $Thr^{669}$ in A431 human epidermoid carcinoma cells (18). TNF-α activates a neutral sphingomyelinase to generate ceramide in HL-60 cells, and it was postulated that this initiated TNF-α action (6). A ceramide-activated protein kinase with a synthetic peptide derived from the amino acid sequence surrounding $Thr^{669}$ of the EGFR (residues 663 to 681) was defined (40). Kinase activity was membrane-associated, $Mg^{2+}$-dependent, and activated by natural or synthetic ceramide in a concentration-and time-dependent manner. This ceramide-activated protein kinase activity was rapidly increased in membranes derived from HL-60 cells treated with TNF-α. The present studies were undertaken to evaluate coupling of this sphingomyelin pathway to stimulation of the TNF receptor in a cell-free system.

The binding of TNF-α to its receptor is detectable within 2 minutes and maximal by 5 to 10 minutes at 4° C. in membranes derived from HL-60 cells (41). Therefore, supernates from HL-60 cells, collected after a low-speed centrifugation to remove nuclei, were first incubated with TNF-α for 5 minutes at 4° C. to allow the formation of TNF-receptor complexes. Thereafter, reactions were initiated by warming supernates to 22° C. in a reaction mixture containing adenosine triphosphate (ATP) and $Mg^{2+}$ at pH 7.4.

These conditions were adopted to allow for activation of neutral sphingomyelinase (1, 42). Under these conditions, TNF-α induced a time- and concentration-dependent reduction in sphingomyelin content (FIG. 9A). the effect of TNF-α was evident at 1 minute and maximal by 7.5 minutes. Sphingomyelin concentrations decreased 27% from a control concentration of $10.4\pm0.5$ (mean ± SEM) to $7.6\pm0.2$ nmol per milligram (nmol $mg^{-1}$) of supernate protein ($P<0.001$). In contrast, the concentration of sphingomyelin in control incubations did not change. Concentrations of TNF-α of 300 pM were ineffective, with a maximal effect at 3 nMTNF-α [effective dose ($ED_{50}$) $\approx$ 500 pM]. Under the same conditions, ceramide increased quantitatively from $1.8\pm0.3$ to $4.0\pm0.5$ nmol $mg^{-1}$ (FIG. 9B). This effect was detectable at 1 minute ($P<0.001$) and maximal by 7.5 minutes. Thus, 2.8 nmol of sphingomyelin per milligram of supernate protein were lost for each 2.2 nmol of ceramide per milligram of supernate protein that was generated. Similar kinetics of sphingomyelin degradation and ceramide generation were determined in intact HL-60 cells (n=3), confirming previous studies (6). Other choline-containing lipids, including phosphatidyl-choline, lysophosphatidylcholine, sphingosylphosphorylcholine(1), and 1,2-diacylglycerol were not affected by TNF-α. Thus, TNF-α activated a neutral sphingomyelinase in a cell-free system, which resulted in the generation of the potential second messenger ceramide.

The effect of TNF-α on ceramide-activated protein kinase activity was assessed. Nuclei-free supernates contain ceramide-activated protein kinase activity that can phosphorylate EGFR peptide with a maximum velocity ($V°_{max}$) of 50 to 100 pmol per minute per milligram (pmol $min^{-1}mg^{-1}$) of protein and a Michaelis constant ($K_m$ of 15 μM) for ATP and 0.25 mg $ml^{-1}$ for peptide (40). Ceramide (0.001 to 3 μM) enhances kinase activity to a maximum of two-fold of the control (40).

Figure 10A:
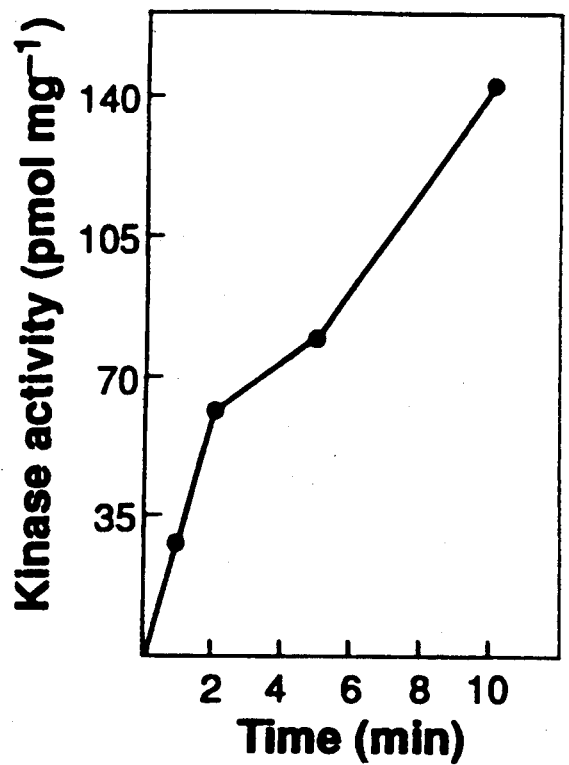
Figure 10B:
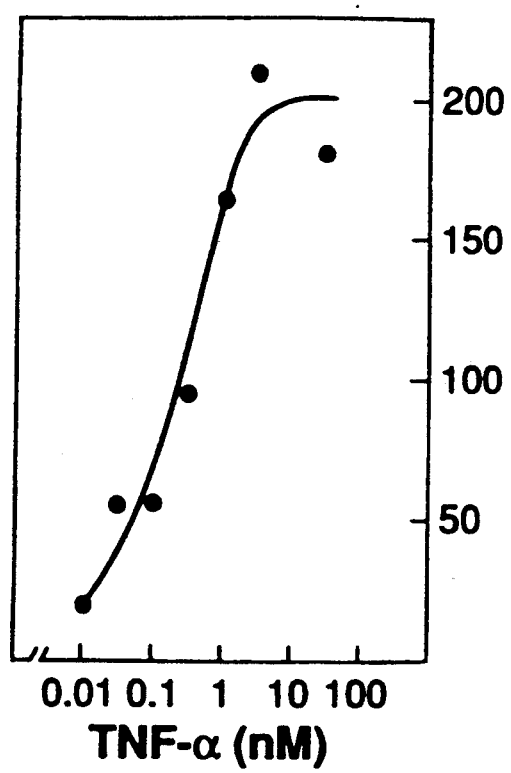

TNF-α, which increased ceramide concentrations, similarly enhanced kinase activity in intact cells (40). For studies assessing the effect of TNFα in broken cell preparations, nuclei-free supernates were incubated under conditions sufficient for stimulation of neutral sphingomyelinase in a reaction mixture that also contained EGFR peptide and γ-$^{32}$P-labeled ATP. Phosphorylated peptide was resolved by high-performance liquid chromatograph (HPLC) and quantified by Cerenkov counting (40). Kinase activity was calculated from the specific activity of [γ-$^{32}$P] ATP and incorporation of $^{32}$P into EGFR peptide. Background activity was subtracted from each point. TNF-α (30 nM) treatment enhanced kinase activity (P<0.001) in a time-dependent manner (FIG. 10A). TNF-α stimulation of kinase activity was evident by 1 minute and demonstrable for at least 10 minutes. If the initial incubation with TNF-α at 4° C. was omitted and TNF was added directly to the reaction mixture at 22° C., the reaction was delayed. Under these conditions, enhancement of activity by TNF-α did not occur for 2 minutes, presumably until after TNF-receptor complexes had formed. TNF-α enhanced kinase activity in a concentration-dependent manner at 5 minutes (FIG. 10B). TNF-α was effective at 10 pM and had a maximal effect at 3 nM; the ED$_{50}$ was ≈300 pM TNF-α. This is similar to the ED$_{50}$ of 200 pM for stimulation of ceramide-activated protein kinase by TNF-α in intact cells (40). TNF-α enhanced kinase activity in a total of 20 separate studies. Guanosine triphosphate (GTP) and guanosine-5'-0-(3-thiotriphosphate) (GTP-γ-S) (0.25 to 200 μM) did not affect kinase activity.

Figure 11:
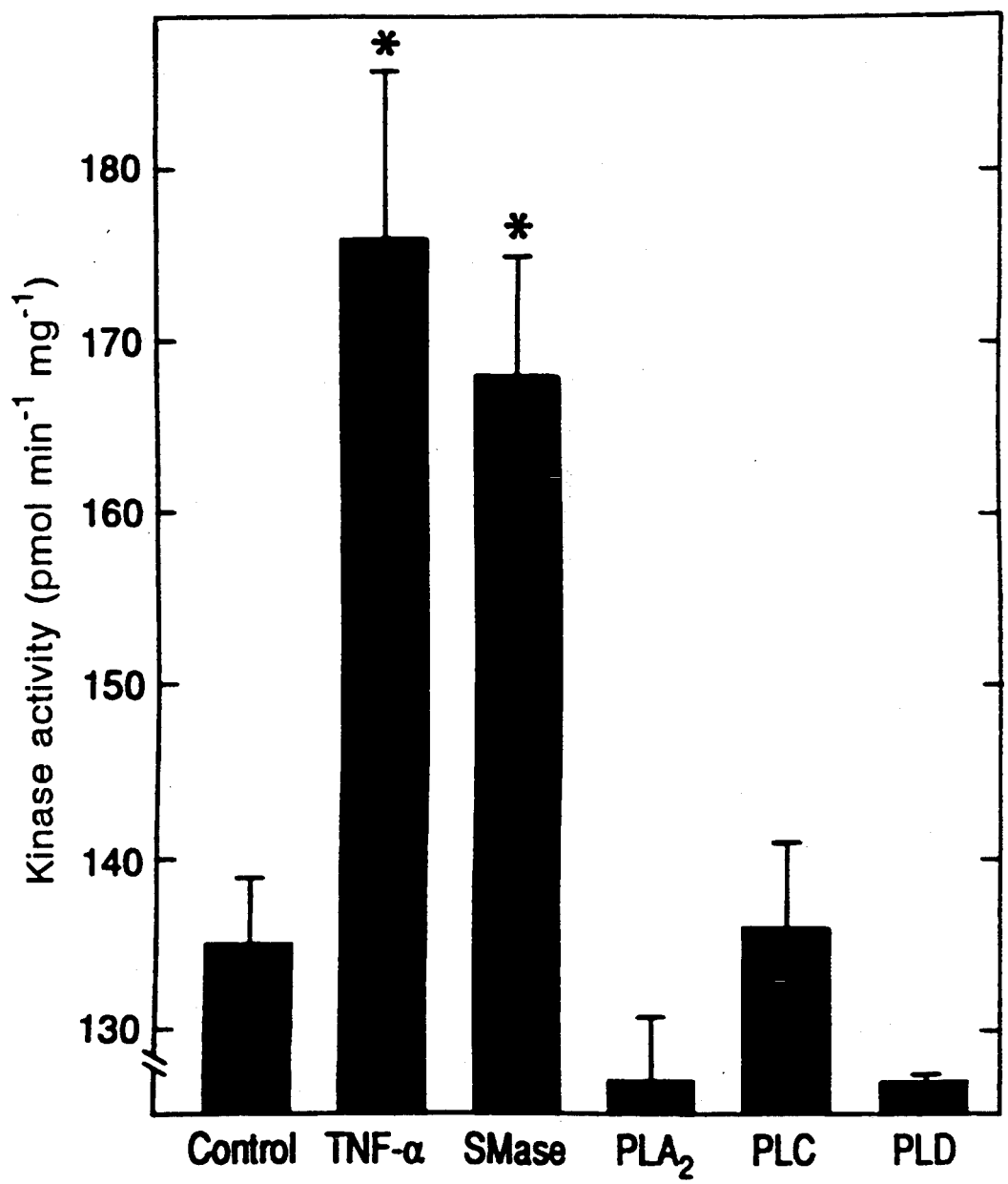

To demonstrate that the effect of TNF-α is mediated by sphingomyelin hydrolysis to ceramide, a sphingomyelinase or a phospholipase (A$_2$, C, or D) was added to the kinase reaction mixture and measured EGFR peptide phosphorylation was measured. For some studies, the reaction mixture contained free Ca$^{2+}$ (1mM), which did not affect results. Control activity reflects several TNF-α-independent protein kinases that are known to phosphorylate EGFR peptide on Thr$^{669}$. Exposure of the nuclei-free supernates to sphingomyelinase (1×10$^{-3}$ U ml$^{-1}$) from *Staphylococcus aureus* for 5 minutes induced and increase in kinase activity comparable to that induced by TNF-α (1 nM) (FIG. 11). This concentration of sphingomyelinase stimulates a two-fold elevation in ceramide levels in HL-60 cells (3, 4). Concentrations of phospholipases A$_2$, C, and D, which were 40- to 400-fold higher than sphingomyelinase and which are effective for phospholipid hydrolysis under conditions used in these assays (43), did not enhance kinase activity. Hence, the effect of TNF-α in broken cell preparations was mimicked by a sphingomyelinase but not by other phospholipases.

The mechanism of coupling of the TNF receptor to sphingomyelinase is unknown. Neutral sphingomyelinase appears to be ubiquitous in mammalian cells and is externally oriented in the plasma membrane (44). Similarly, sphingomyelin is preferentially localized to the outer leaflet of the plasma membrane (45). This colocalization of receptor, phospholipase, and substrate at the plasma membrane suggests that ceramide is generated at this site. The exact intracellular site of the ceramide-activated protein kinase has not yet been investigated. However, preliminary evidence suggests it is an intrinsic membrane protein (40). In this regard, ceramide-activated protein kinase would not have to be present in the outer leaflet of the plasma membrane for signaling to occur, as ceramide can redistribute across a membrane bilayer (46).

Ceramide-activated protein kinase may be a member of an emerging family of serine/threonine protein kinases that includes microtubule-associated protein 2 (MAP2) kinase [extracellular signal-regulated kinase (ERK1)] (35, 47, 48), EGFR threonine (ERT) kinase (49), glycogen synthase kinase-3 (35, 47, 48) and p34$^{cdc2}$-containing proline-directed and histone H1 kinases (49, 50). The substrates for these kinases appear to have a minimal recognition sequence, X-Ser/Thr-Pro-X, in which the phosphorylated site is flanked by a COOH-terminal proline residue (50, 51) and X can be any amino acid. Substrates for this class of kinases include EGFR, proto-oncogene products Jun and Myc, tyrosine hydroxylase, histone H1, glycogen synthase, synapsin I, and protein phosphatase inhibitor II (37, 49–51). TNF-induced, proline-directed phosphorylation of these proteins has not yet been demonstrated. The X-Ser/Thr-Pro-X sequence is different from consensus substrate sequences for other major serine/threonine kinases, including cyclic adenosine monophosphate (cAMP)- and cyclic guanosine monophosphate (cGMP)-dependent-protein kinases, Ca$^{2+}$/calmodulin-dependent-protein kinase, and ribosomal S6 protein kinase (49). In fact, these kinases have limited activity toward this proline-containing sequence (50).

It has been proposed that various distinct signaling systems, including protein kinases A and C, phospholipases A$_2$ and C, the EGFR tyrosine kinase, and a novel serine kinase, may mediate TNF-α action (19). It is clear that no single second messenger pathway can account for the entirety of the reported biologic effects of TNF-α. The role of the sphingomyelin pathway in events other than monocytic differentiation has not been investigated nor has the relation to these other signaling systems. This issue is further complicated by the recent cloning of two distinct TNF receptor forms of 55 kD and 75 kD (52–55) with homologous extracellular domains with dissimilar intracellular portions.

In sum, the rapid kinetics of activation of the sphingomyelin pathway by TNF-α in intact cells, the ability of cell-permeable ceramide analogs to bypass receptor activation and mimic TNF-α action, and the reconstitution of this cascade in a cell-free system provide strong support for the notion that this pathway serves to couple TNF receptor activation to cellular stimulation. Hence, these studies suggest that TNF-α activates a plasma membrane-bound neutral sphingomyelinase to generate at the second messenger ceramide, which stimulates the ceramide-activated protein kinase to phosphorylate a distinct set of protein substrates, thereby altering their function.

III - Interleukin-1β Signals Through the Sphingomyelin Pathway in Intact EL-4 Cells and in a Cell-Free System A. Abstract The mechanism of interleukin-1 (IL-1) signaling is unknown. Recent investigations demonstrated that tumor necrosis factor-α utilizes a signal transduction pathway involving sphingomyelin hydrolysis to ceramide and stimulation of a ceramide-activated protein kinase. In intact EL-4 thymoma cells, IL-1β similarly stimulated rapid reduction in sphingomyelin and elevation in ceramide levels, and enhanced ceramide-activated protein kinase activity. This cascade was also activated by IL-1β in a cell-free system demonstrating tight coupling to the receptor. Further, exogenous sphingomyelinase but not phospholipases $A_2$, C or D, replaced IL-1β to stimulate IL-2 secretion in combination with phorbol ester. These studies demonstrate that IL-1β signals through the sphingomyelin pathway.

B. Experimental Methods and Discussion

Hydrolysis of sphingomyelin to ceramide at the plasma membrane by a neutral sphingomyelinase may initiate a cascade that functions in signaling (6–8, 18, 40, 58, 59). Evidence has been provided that ceramide may stimulate a serine/threonine kinase termed ceramide-activated protein kinase to transduce the signal (18, 40, 59). Ceramide-activated protein kinase is membrane-bound, $Mg^{+2}$-dependent and defined by its capacity to phosphorylate a synthetic peptide derived from the amino acid sequence surrounding $Thr^{669}$ of the epidermal growth factor receptor (EGFR). Ceramide-activated protein kinase may be a member of an emerging family of proline-directed serine/threonine kinases that includes the extracellular-signal regulated (also referred to as nitogen-activated) and $p34^{cdc2}$ kinases (47). Substrates for these kinases contain the minimal recognition sequence, X-Ser/Thr-Pro-X, in which the phosphorylated site is flanked on its carboxy terminus by a proline residue and X can be any amino acid.

Evidence has been provided that tumor necrosis factor (TNF)-α may utilize the sphingomyelin pathway for signaling (6, 40, 59). TNF stimulates this pathway early during HL-60 cell differentiation into monocytes (6, 59) and synthetic ceramide analogs bypass receptor activation and directly induce differentiation (7). Further, this cascade has been reconstituted in a cell-free system comprised of extracts of HL-60 cells, demonstrating tight coupling of this pathway to the TNF receptor (59). The present studies were performed because of numerous reports that TNF and IL-1 stimulate a common set of events in diverse biologic systems (60).

The murine thymoma EL-4 cell line is a well-defined IL-1 responsive cell line that expresses functional IL-1 receptors (61, 62). Upon stimulation with IL-1, these cells up-regulate the IL-2 receptor and secrete IL-2 (62). Initial studies were designed to investigate the effects of IL-1β on cellular sphingomyelin content. Cells, grown in Dulbecco's Modified Eagle's (DME)/Ham's F-12 medium containing 10% horse serum and [$^3$H]choline (1 μCi ml$^{-1}$), were resuspended back into the same medium at $10 \times 10^6$ cells ml$^{-1}$ and stimulated with IL-1β. IL-1β is commercially available. Under these conditions, IL-1β induced time- and concentration-dependent sphingomyelin hydrolysis (FIGS. 12A and 12B). A maximally effective concentration of IL-1β, 40 ng ml$^{-1}$ induced a detectable reduction in sphingomyelin content by 2 minutes from a baseline of $800 \pm 14$ pmol $10^6$ cells$^{-1}$ (mean $\pm$ SEM) and the level decreased to $648 \pm 16$ pmol $10^6$ cells$^{-1}$ (p<0.005) at 30 minutes. Concentrations of IL-1β of 0.01 ng ml$^{-1}$ were effective, with a maximal effect at 10 ng ml$^{-1}$ [effective dose ($ED_{50}$)≈2 ng ml$^{-1}$ (FIG. 12B)]. A similar reduction in sphingomyelin content after IL-1 stimulation was determined by direct measurement of phosphorous content (63). In contrast, the content of phosphatidylcholine, the other major choline-containing phospholipid, was unchanged.

Under the same conditions, IL-1β induced a statistically significant increase in ceramide content (FIG. 13). Ceramide increased from 360 to 403 pmol $10^6$ cells$^{-1}$ at 2 minutes (p<0.005) and to a maximum of 450 pmol $10^6$ cells$^{-1}$ at 15 minutes. In separate studies (n=4), a statistically significant increase in ceramide content was evident by 30 seconds. Maximally effective concentrations of other agents known to stimulate EL-4 cells (65, 66) including 12-0-tetradecanoylphorbol-13-acetate (TPA), concanavalin A, epinephrine and an anti-CD3 antibody failed to elicit a ceramide response (n=5). Hence, sphingomyelinase activation appeared specific for stimulation by IL-1β. Subsequent studies assessed whether IL-1β also enhanced ceramide-activated protein kinass activity. EL-4 cells were found to contain a membrane-bound ceramide-activated protein kinass activity similar to that reported in A431 human epidermoid carcinoma cells and HL-60 cells (40, 59). Activity was measured by the transfer of $^{32}$P from the γ-position of ATP to EGFR peptide (AA 663–681 of the EGFR). The effect of IL-1β on kinase activity was determined using microsomal membranes derived from cells stimulated with IL-1β. IL-1β enhanced kinase activity in a time- and concentration-dependent manner. In cells treated with 10 ng ml$^{-1}$ IL-1β, a maximally effective concentration, an increase in kinase activity was detectable at 30 seconds (data not shown) and maximal at 2 minutes (FIG. 14, p<0.005). Activity increased to 2.1-fold of control from 5 to 11 pmol per minute per milligram (pmol min$^{-1}$ mg$^{-1}$) and then gradually declined over 15 minutes. Concentrations of IL-1β of 0.03 ng ml$^{-1}$ were effective, with a maximal effect at 10 ng ml$^{-1}$ [effective dose ($ED_{50}$)≈2 ng ml$^{-1}$]. This is the same range of concentrations found effective for sphingomyelin hydrolysis. Stimulation by IL-1β was detected in a total of 10 experiments. Cytosolic fractions of EL-4 cells also contained kinase activity toward EGFR peptide of 2.6 $\pm$0.3 (mean $\pm$ range) pmol min$^{-1}$ mg$^{-1}$. Cytosolic ac which represents proline-directed protein kinase activities other than ceramide-activated protein (68), was not enhanced by Ii-1β during these studies. Further, protein kinase C activity as determined by phosphorylation of lysine-rich histone (Sigma Chem. Co., type III-S)(69) was not enhanced in either membrane or cytosolic fractions.

Early kinetics of activation of a potential signaling system provide some support that the pathway might be involved in the signaling process. However, signal transduction pathways are highly regulated and often interrelated (70). Hence, activation of one system often results in rapid activation of another. To provide additional support for tight coupling of the sphingomyelin pathway to activation of the IL-1β receptor, studies were performed with subcellular fractions derived from EL-4 cells. For these studies, supernates, collected after a low-speed centrifugation to remove nuclei, were first incubated with IL-1β for 10 minutes at 4° C. to permit formation of IL-1 receptor complexes (59). Thereafter, reactions were initiated by warming supernates to 22° C. in a reaction mixture containing $Mg^{2+}$ at pH 7.4. These conditions were adopted to allow for activation of endogenous neutral sphingomyelinase (1, 42). For studies measuring kinase activity, reaction mixtures also contained [$^{32}$P] ATP and EGFR peptide. Under these conditions, IL-1β stimulated a rapid reduction in sphingomyelin content and a quantitative increase in ceramide content (FIG. 15A). In separate studies, a statistically significant reduction in sphingomyelin content (n=10) and elevation in ceramide content (n=6) were detected at i minute of stimulation (p<0.005 vs. control). Ceramide-activated protein kinase activity also increased (FIG. 15B). These effects were quantitatively similar to those determined in the intact cells. Hence, the effect of IL-1β to activate the sphingomyelin pathway was also observed in a cell-free system.

To determine whether the sphingomyelin pathway mediated the biologic response to IL-1β, direct activation of the sphingomyelin pathway with exogenous sphingomyelinase (59) was compared to stimulation by IL-1β. For these studies, cells were treated with IL-1β, sphingomyelinase and/or phorbol ester and, after 24 h IL-2 secreted into the media was measured. As previously reported (62, 65, 71, 72), IL-1β (1–30 ng ml$^{-1}$) alone did not induce detectable IL-2 secretion (Table 1), nor did TPA (1–20 ng ml$^{-1}$) alone. However, in combination IL-1β (10 ng ml$^{-1}$) and TPA (20 ng ml$^{-1}$) stimulated secretion maximally. Sphingomyelinase alone also failed to stimulate IL-2 secretion, but again, in combination with TPA, induced secretion. Concentrations of sphingomyelinase between $5 \times 10^{-5}$ U ml$^{-1}$ and $1 \times 10^{-1}$ U ml$^{-1}$ were effective. In separate studies (n=2), sphingomyelinase ($1 \times 10^{-3}$ U ml$^{-1}$) induced secretion at all concentrations of TPA from 0.5 to 20 ng ml$^{-1}$. This concentration of sphingomyelinase induced an increase in ceramide content quantitatively similar to that induced by maximally effective concentrations of IL-1β, and has previously been shown to mimic TNF action in HL-60 cells (59). In contrast, phospholipases (PL) A$_2$, C and D at concentrations 10–50 times higher than maximally effective sphingomyelinase, did not stimulate IL-2 secretion alone or in combination with TPA. Hence, the effect of IL-1 to co-stimulate IL-2 secretion in EL-4 cells was mimicked by activation of the sphingomyeline pathway with sphingomyelinase.

Table I

Induction of IL-2 secretion by IL-1 and sphingomyelinase

EL4 cells ($1.5 \times 10^6$ ml$^{-1}$) were treated with IL-1β (10 ng ml$^{-1}$), sphingomyelinase (SMase, *Staphylococcus aureus*), PLA$_2$ (*Vipera ruseill*), PLC (*Bacillus cereus*) and PLD (*Streptomyces chromofuscus*) at the indicated concentrations, in the absence or presence of TPA (20 ng ml$^{-1}$). Boiled sphingomyelinase preparations had no activity. Culture supernates were harvested at 24 h and assayed for secreted IL-2 using an anti-mouse IL-2 ELISA kit (Genzyme Corp.) according to the manufacturer's instructions. The lower limit of sensitivity of this assay was 15 pg IL-2 and the assay was linear up to 960 pg IL-2. These data (mean ± range) represent duplicate determinations from 2 experiments.

|  | Diluent | ±TPA |
| --- | --- | --- |
| Control | nd* | nd |
| IL-1β (10 ng ml$^{-1}$) | nd | 261 ± 2 |
| SMase (1 × 10$^{-3}$ u ml$^{-1}$) | nd | 313 ± 60 |
| PLA$_2$ (1–5 × 10$^{-2}$ u ml$^{-1}$) | nd | nd |
| PLC (1–5 × 10$^{-2}$ u ml$^{-1}$) | nd | nd |
| PLD (1–5 × 10$^{-2}$ u ml$^{-1}$) | nd | nd |

*nd, not detectable

Although signaling for IL-1 has been ascribed to various protein kinases including protein kinases A and C and a novel serine/threonine protein kinase (30, 73–77), no coherent picture has emerged to account for all of the data. Two distinct IL-1 receptors of 60 kDa and 80 kDa have recently been cloned (78–80). The receptors are homologous in their extracellular binding domains but have little homology in their cytoplasmic portions. In fact the 60 kDa receptor has only a short intracellular portion. There is no empiric or structural evidence suggesting that these receptors themselves might serve as protein kinases (78–80). In addition, there is no homology between these receptors and any protein known to be involved in signal transduction. The present studies define a new mechanism by which the IL-1 receptor might activate a protein kinase. Preliminary studies with the human natural killer-like cell line, YT (81), demonstrate that IL-1 also induces rapid generation of ceramide in this system.

Despite the often reported similarities in action of TNF-α and IL-1 there is limited primary sequence homology between their receptors. Hence, the mechanism by which these two cytokines activate the sphingomyelin signal transduction pathway is not readily apparent. In sum, these studies provide evidence that the effects of IL-1β may be mediated by the sphingomyelin signal transduction pathway. In this paradigm, ligand binding to the receptor activates a neutral sphingomyelinase hydrolysing sphingomyelin to ceramide. Neutral sphingomyelinase appears to be ubiquitous in mammalian cells and like sphingomyelin is externally oriented in the plasma membrane (44). This co-localization of receptor, phospholipase and substrate at the plasma membrane suggests that ceramide is generated at this site. Ceramide, which can redistribute across a lipid bilayer, then stimulates ceramide-activated protein kinase which phosphorylates a specific subset of cellular proteins thereby altering their function.

REFERENCES

1. Kolesnick, R. N., J. Biol. them. 262: 16759–16762 (1987).

2. Kolesnick, R. N. and Clegg, S., J. Biol. Chem. 263: 6534–6537 (1988).

3. Kolesnick, R. N., J. Biol. Chem. 264:7617–7623 (1989).

4. Dressier, K. A. and Kolesnick, R. N., J. Biol. Chem. 265:14917–14921 (1990).

5. Kolesnick, R. N. and Hemer, M. R., J. Biol. Chem. 265:18803–18808 (1990).

6. Kim, M.-Y., Linardic, C., Obeid, L. and Hannun, Y., J. Biol. Chem. 266:484–489 (1991).

7. Okazaki, T., Bielawska, A., Bell, R. M. and Hannun, Y. A., J. Biol. Chem. 265:15823–15831 (1990).

8. Okazi, T., Bell, R. M. and Hannun, Y. A., J. Biol. Chem. 264:19076–19080 (1989).

9. Hannun, Y. A., Loomis, C. R., Merill, A. H., Jr., and Bell, R. M., J. Biol. Chem. 261:12604–12609 (1986).

10. Merrill, A. H., Jr., Sereni, A. M., Stevens, V. L., Hannun, Y. A., Bell, R. M. and Kinkade, J. M., Jr., J. Biol. Chem. 261:12610–12615 (1986).

11. Wilson, E., Olcott, M. C., Bell, R. M., Merril, A. H., Jr., and Lambeth, J. D., J. Biol. Chem. 261:12616–12623 (1986).

12. Hannun, Y. and Bell, R. M., Science 235:670–674 (1987).

13. Bajjalieh, S. M., Martin, T. F. J. and Floor, E., J. Biol. Chem. 264:14354–14360 (1989).

14. Slife, C. W., Wang, E., Hunter, R., Burgess, C., Liotta, D. and Merrill, A. H., Jr., J. Biol. Chem 264:1–7 (1989).

15. Faucher, M., Girones, N., Hannun, Y. A., Bell, R. M. and Davis, R. J., J. Biol. Chem. 263:5319–5327 (1988).

16. Davis, R. J., Girones, N. and Faucher, M., J. Biol. Chem. 263:5373–5379 (1988).

17. Countaway, J. L., Northwood, I. C. and Davis, R. J., J. Biol. Chem. 264:10828–10835 (1989).

18. Goldkorn, T., Dressler, K. A., Muindi, J., Radin, N. S., Mendelsohn, J., Menaldino, D., Liotta, D. and Kolesnick, R. N., J. Biol. Chem. 266:16092–16097 (1991).

19. Vilcek, J., and Lee, T. H., J. Biol. Chem. 266:7313–7316 (1991).

20. Schutze, S., Scheurich, P., Pfizenmaier, K. and Kronke, M., J. Biol. Chem. 264:3562–3567 (1989).

21. Robaye, B., Hepburn, A., Lecocq, R., Fiers, W., Boeynaems, J.-M. and Dumont, J. E., Biochem. Biophys. Res. Commun. 163:301–308 (1989).

22. Marino, M. W., Feld, L. J., Jaffe, E. A., Pfeffer, L. M., Hanm H. -M. and Donner, D. B., J. Biol. Chem. 266:2685–2688 (1991).

23. Marino, M. W., Pfeffer, L. M., Guidon, P. T., Jr. and Donner, D. B., Proc. Natl. Acad. Sci. USA 86:8417–8421 (1989).

24. Donato, N. J., Gallick, G. E., Steck, P. A. and Rosenblum, M. G., J. Biol. Chem. 264: 20474–20481 (1989).

25. Bowen, S., Stanley, K., Selva, E. and Davis, R. J., J. Biol. Chem. 266:1162–1196 (1991).

26. Cooper, J. A., Septon, B. B. and Hunter, T., Methods Enzymol. 99:387–402 (1983).

27. Bradford, M. M., Anal. Biochem. 72:248–254 (1976).

28. Chaplinski, T. J. and Niedel, J. E., J. Clin. Invest. 70:953–964 (1982).

29. Breitman, T. R., Selonick, S. E. and Collins, S. J., Proc. Natl. Acad. Sci. USA 77:2936–2940 (1980).

30. Zhang, Y., Lin, J.-X., Yip, Y. K. and Vilek, J., Proc. Natl. Acad. Sci. USA 85:6802–6805 (1988).

31. Kronke, M., Schutze, S., Scheurich, R. and Pfizenmaier, K. in "Tumor Necrosis Factor: Structure, Function and Mechanism of Action," eds. Aggarwal, B. B. and Vilcek, J. (Dekker, New York), pp.189–216 (1991).

32. Brenner, D. A., O'Hara, M., Angel, P., Chojkier, M. and Karin, M., Nature (London) 337:661–663 (1989).

33. Shiroo, M. and Matsushima, K., Cytokine 2: 13–20 (1990).

34. Edelman, A. M., Blumenthal, D. K. and Krebs, E. G., Annu. Rev. Blochem. 56:567–613 (1987).

35. Heisermann, G. J. and Gill, G. N., J. Biol. Chem. 263:13152–13158 (1988).

36. Heisermann, G. J., Wiley, H. S., Walsh, B. J., Ingraham, H. A., Fiol. C. J. and Gill, G. N., J. Biol. Chem. 265:12820–12827 (1990).

37. Aitken, A., Holmes, C. F. B., Campbell, D. G., Resink, T. J., Cohen, P., Leung, C. T. W. and Williams, D. H., Biochim. Biophys. Acta. 790:288–291 (1984).

38. Carpenter, G. and Cohen, S., J. Biol. Chem. 265:7709–7712 (1990).

39. R. N. Kolesnick, Prog. Lipid Res. 30, 1 (1991).

40. S. Mathias, K. A. Dressler, R. N. Kolesnick, Proc. Natl. Acad. Sci USA 88, 10009 (1991).

41. K. Imamura, M. L. Sherman, D. Spriggs, D. Kufe, J. Biol. Chem. 263, 10247 (1988).

42. B. G. Rao and M. W. Spence, J. Lipid Res. 17, 506 (1976).

43. D. V. M. Das, H. W. Cook, M. W. Spence, Biochim. Biophys. Acta 777, 339 (1984).

44. Y. Barenholz and T. E. Thompson, Biochim. Biophys. Acta 604, 129 (1980).

45. N. G. Lipsky and R. E. Pagano, Cell Biol. 80, 2608 (1983).

46. R. Seger et al., Proc. Natl. Acad. Sci USA 88, 6142 (1991).

47. T. G. Boulton et al., Science 249, 64 (1990).

48. I. C. Northwood, F. A. Gonzalez, M. Wartmann, D. L. Raden, R. J. Davis, J. Biol. Chem. 266, 15266 (1991).

49. F. L. Hall et al., J. Biol. Chem. 266, 17430 (1991).

50. E. Alvarez et al., J. Biol. Chem. 266, 15277 (1991).

51. H. Loetscher et al., Cell 61, 351 (1990).

52. T. Schall et al., J. Biol. Chem.351, 361 (1990).

53. C. A. Smith et al., Science 248, 1019 (1990).

54. Z. Dembic et al., Cytokine 2, 231 (1990).

55. K. A. Dressler, C.-C. Kan, R. N. Kolesnick, J. Biol. Chem. 266, 11522 (1991).

56. J. Preiss et al., J. Biol. Chem. 261, 8597 (1986).

57. R. N. Kolesnick, Trends in Cell Biol. (in press).

58. K. A. Dressier, S., Mathias, R. N., Kolesnick, Science 255, 1715 ( 1992 ).

59. R. Neta, T. J. Sayers, J. J. Oppenheim, in "Tumor Necrosis Factors: Structure, Function and Mechanism of Action" pp. 499–566 (eds. B. B. Aggarwal, J. Vilcek) Marcel Dekker, Inc., NY, N.Y. (1992).

60. S. K. Dower et al., J. Exp. Med. 162, 501 (1985).

61. J. W. Lowenthal, J-C Cerottini, H. R. MacDonald, J. Immunol. 137, 1226 (1986).

62. P. S. Chen, Jr., T. Y. Toribora, H. Warner, Anal. Chem. 28, 1756 (1956).

63. M. J. Rebecchi, R. N. Kolesnick, M. C. Gershengorn, J. Biol. Chem. 258, 227 (1983).

64. J. J. Farrar et al., J. Immunol. 125, 2555 (1980).

65. L. A. J. O'Neill, T. A. Bird, A. J. H. Gearing, J. Saklatvala, J. Biol. Chem. 265, 3146 (1990).

66. J. Dornand, C. Sekkat, J.-C. Mani, M. Gerber, Immunol. Lett. 16, 101 (1987).

67. T. A. Bird, P. R. Sleath, P. C. deRoos, S. K. Dower, G. D. Virca, J. Biol. Chem. 266, 22661 (1991).

68. R. Ballester, O. H. Rosen, J. Biol. Chem. 260, 15194 (1985).

69. Y. Nishizuka, J. Am. Med. Assoc. 262, 1826 (1989).

70. I. von Hoegen, W. Falk, G. Kojouharoff, P. H. Krammer, Eur. J. Immunol. 19, 329 (1989).

71. J. Dornand et al., J. Cell Physiol. 151, 71 (1992).

72. F. Shirakawa, U. Yamashita, M. Chedid, S. B. Mizel, Proc. Natl. Acad. Sci. 85, 8201 (1988).

73. M. Chedid, F. Shirakawa, O. Naylor, S. Mizel, J. Immunol 142, 4301 (1989).

74. E. Munoz, U. Beutner, A. Zubiaga, T. Huber, J. Immunol. 144,964 (1990) .

75. T. A. Bird, J. Saklavata, J. Immunol. 142,126 (1989).

76. L. A. J. O'Neill, T. A. Bird, J. Saklatvala, Immunol. Today 11, 392 (1990).

77. J. E. Sims et al., Science 241, 585 (1988).

78. J. E. Sims et al., Proc. Natl. Acad. Sci. USA 86, 8946 (1989).

79. C. J. Mcmahan et al., EMBO J. 10, 2821 (1991).

80. J. Yodoi et al., J. Immunol. 134, 1623 (1985).

81. R. N. Kolesnick, A. Paley, J. Biol. Chem. 262, 9204 (1987).

---

What is claimed is:

1. A purified membrane-bound ceramide-activated protein kinase obtained from human cells, said kinase has a molecular weight of about 95 kD as determined using a denaturing gel method and specifically phosphorylates the threonine residue in a Pro-Leu-Thr-Pro-containing polypeptide.

* * * * *